United States Patent
Sasikumar et al.

(10) Patent No.: US 9,422,339 B2
(45) Date of Patent: Aug. 23, 2016

(54) IMMUNOMODULATING CYCLIC COMPOUNDS

(71) Applicants: Pottayil Govindan Nair Sasikumar, Bangalore (IN); Muralidhara Ramachandra, Bangalore (IN)

(72) Inventors: Pottayil Govindan Nair Sasikumar, Bangalore (IN); Muralidhara Ramachandra, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 14/388,584

(22) PCT Filed: Mar. 28, 2013

(86) PCT No.: PCT/IB2013/000553
§ 371 (c)(1),
(2) Date: Sep. 26, 2014

(87) PCT Pub. No.: WO2013/144704
PCT Pub. Date: Oct. 3, 2013

(65) Prior Publication Data
US 2015/0125491 A1 May 7, 2015

(30) Foreign Application Priority Data

Mar. 29, 2012 (IN) .......................... 1213/CHE/2012

(51) Int. Cl.
*C07K 7/64* (2006.01)
*A61K 45/06* (2006.01)
*A61K 38/12* (2006.01)
*C07K 14/705* (2006.01)
*C07K 14/47* (2006.01)
*A61K 31/395* (2006.01)
*A61K 38/00* (2006.01)

(52) U.S. Cl.
CPC .............. *C07K 7/64* (2013.01); *A61K 31/395* (2013.01); *A61K 38/12* (2013.01); *A61K 45/06* (2013.01); *C07K 14/4747* (2013.01); *C07K 14/70503* (2013.01); *A61K 38/00* (2013.01)

(58) Field of Classification Search
None
See application file for complete search history.

(56) References Cited

FOREIGN PATENT DOCUMENTS

| | | |
|---|---|---|
| EP | 1537878 A1 | 8/2005 |
| WO | 01/14557 A1 | 3/2001 |
| WO | 02/079499 A1 | 10/2002 |
| WO | 02/086083 A2 | 10/2002 |
| WO | 03/042402 A2 | 5/2003 |
| WO | 2004/056875 A1 | 7/2004 |
| WO | 2011/161699 A2 | 12/2011 |

OTHER PUBLICATIONS

Asquith et al., Angew. Chem. Internat. Edu. (1974) 13, 514-520.*
Thermo Technical Information, N-Terminal Acetylation and C-Terminal Amidation of Peptides (2004) available at http://www.greiner-bio-one.co.jp/products/peptides/acetylation_amidation.pdf., accessed on Sep. 29, 2015.*
Yasutoshi Agata et al. Expression of the PD-1 antigen on the surface of stimulated mouse T and B lymphocytes. International Immunology, 1996, vol. 8 : p. 765; entire document.
Joseph Illingworth et al. Chronic Exposure to Plasmodium falciparum Is Associated with Phenotypic Evidence of B and T Cell Exhaustion. Journal of Immunology, 2013, vol. 190: pp. 1038-1047; entire document.
Suzanne L. Topalian et al. Safety, Activity, and Immune Correlates of Anti-PD-1 Antibody in Cancer. N Engl J Med. 2012, vol. 366: pp. 2443-2454; entire document.
Julie R. Brahmer et al. Safety and Activity of Anti-PD-L1 Antibody in Patients with Advanced Cancer. N Engl J Med. 2012, vol. 366: pp. 2455-2465; entire document.
Ludmila Prokunina et al. A regulatory polymorphism in PDCD1 is associated with susceptibility to systemic lupus erythematosus in humans. Nature Genetics, 2002, vol. 32: pp. 666-669; entire document.

* cited by examiner

*Primary Examiner* — Marcela M Cordero Garcia
*Assistant Examiner* — Catherine Mader
(74) *Attorney, Agent, or Firm* — Benjamin Aaron Adler

(57) ABSTRACT

The present invention relates to novel cyclic compounds as therapeutic agents capable of inhibiting the programmed cell death 1 (PD1) signalling pathway. The invention also relates to derivatives of the therapeutic agents. The invention also encompasses the use of the said therapeutic agents and derivatives for treatment of disorders via immunopotentiation comprising inhibition of immunosuppressive signal induced due to PD-1, PD-L1, or PD-L2 and therapies using them.

31 Claims, 1 Drawing Sheet

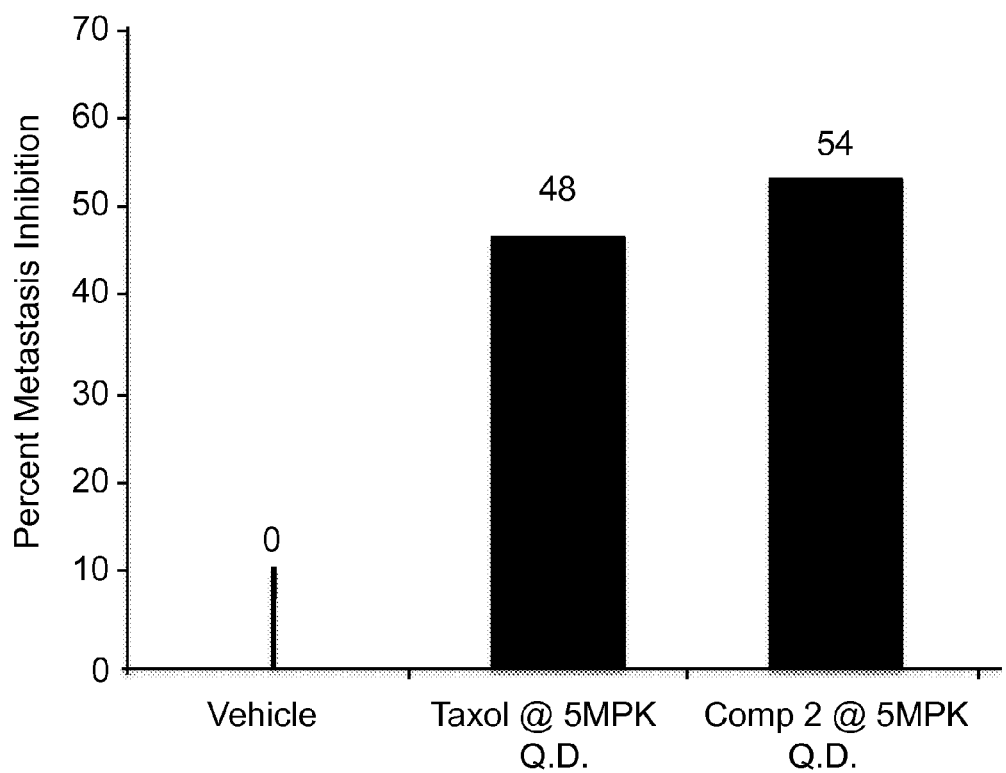

```
SEQUENCE LISTING

<160> NUMBER OF SEQ ID NOS: 36

<210> SEQ ID NO 1
<211> LENGTH: 137
<212> TYPE: PRT
<213> ORGANISM: Homo sapiens
<220> FEATURE:
<221> NAME/KEY: PEPTIDE
<223> OTHER INFORMATION: Extracellular domain of Human PD1

<400> SEQUENCE: 1

Pro Pro Thr Phe Ser Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
            20                  25                  30

Asn Trp Tyr Arg Met Ser Pro Ser Asn Gln Thr Asp Lys Leu Ala Ala
        35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg Val Thr
            100                 105                 110

Glu Arg Arg Ala Glu Val Pro Thr Ala His Pro Ser Pro Ser Pro Arg
        115                 120                 125

Ser Ala Gly Gln Phe Gln Thr Leu Val
    130                 135

<210> SEQ ID NO 2
<211> LENGTH: 7
<212> TYPE: PRT
<213> ORGANISM: Homo sapiens
```

```
<220> FEATURE:
<221> NAME/KEY: PEPTIDE
<223> OTHER INFORMATION: BC Loop

<400> SEQUENCE: 2

Ser Asn Thr Ser Glu Ser Phe
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 3

Ser Lys Thr Ser Glu Ser Phe
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 4

Ser Glu Thr Ser Lys Ser Phe
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 5

Ser Asn Thr Ser Glu Ser Phe
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic Peptide
```

```
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 6

Glu Glu Thr Ser Lys Ser Phe
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Ile at residue 7 is amidated

<400> SEQUENCE: 7

Ser Glu Thr Ser Lys Ser Ile
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 8

Ile Glu Thr Ser Lys Ser Phe
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 9

Ser Glu Thr Ser Lys Val Phe
1               5

<210> SEQ ID NO 10
```

```
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Val at residue 7 is amidated

<400> SEQUENCE: 10

Ser Glu Thr Ser Lys Ser Val
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 11

Ser Glu Thr Ser Lys Ile Phe
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 12

Val Glu Thr Ser Lys Ser Phe
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge

<400> SEQUENCE: 13

Ile Glu Met Ser Lys Ser Gln
1               5
```

```
<210> SEQ ID NO 14
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge

<400> SEQUENCE: 14

Ile Glu Met Ser Lys Val Gln
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 15

Ser Glu Met Ser Lys Ser Phe
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge

<400> SEQUENCE: 16

Ser Asn Thr Ser Glu Ser Phe Gln
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..8
<223> OTHER INFORMATION: Cyclic Bridge
<220> FEATURE:
<221> NAME/KEY: SITE
<222> LOCATION: 7..8
<223> OTHER INFORMATION: -NH-(CH2)5-CO- linked between C-terminal of
      Phe 7 and N-terminal of Glu 8

<400> SEQUENCE: 17

Ser Asn Thr Ser Glu Ser Phe Gln
1               5

<210> SEQ ID NO 18
<211> LENGTH: 8
```

```
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..8
<223> OTHER INFORMATION: Cyclic Bridge

<400> SEQUENCE: 18

Ser Glu Thr Ser Lys Ser Phe Gln
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..8
<223> OTHER INFORMATION: -CO-(CH2)5-NH2- linked between N-terminal of
      Ser 1 and C-terminal of Gln 8, which forms a Cyclic Bridge

<400> SEQUENCE: 19

Ser Glu Thr Ser Lys Ser Phe Gln
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..8
<223> OTHER INFORMATION: -CO-(CH2)5-NH2- linked between N-terminal of
      Ser 1 and C-terminal of Gln 8, which forms a Cyclic Bridge

<400> SEQUENCE: 20

Ser Asn Thr Ser Glu Ser Phe Gln
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..8
<223> OTHER INFORMATION: -CO-(CH2)5-NH2- linked between N-terminal of
      Ser 1 and gamma C-terminal of Glu 8, which forms a Cyclic Bridge
<220> FEATURE:
<221> NAME/KEY: SITE
<222> LOCATION: 8
<223> OTHER INFORMATION: Glu at residue 8 is amidated

<400> SEQUENCE: 21

Ser Asn Thr Ser Glu Ser Phe Glu
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic Peptide
```

```
<220> FEATURE:
<221> NAME/KEY: SITE
<222> LOCATION: 1..8
<223> OTHER INFORMATION: Cyclic Bridge between N-terminal of Ser 1 and
      gamma C-terminal of Glu 8
<220> FEATURE:
<221> NAME/KEY: SITE
<222> LOCATION: 8
<223> OTHER INFORMATION: Glu at residue 8 is amidated

<400> SEQUENCE: 22

Ser Glu Thr Ser Lys Ser Phe Glu
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Tyr at residue 7 is amidated

<400> SEQUENCE: 23

Ser Glu Thr Ser Lys Ser Tyr
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..6
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 24

Ser Glu Thr Ser Ser Lys Phe
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge

<400> SEQUENCE: 25

Ser Glu Thr Ser Lys Ser Phe
1               5

<210> SEQ ID NO 26
<211> LENGTH: 8
<212> TYPE: PRT
<213> ORGANISM: Artificial sequence
```

```
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 8
<223> OTHER INFORMATION: Lys at residue 8 is amidated

<400> SEQUENCE: 26

Ser Glu Thr Ser Lys Ser Phe Lys
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Glu at residue 7 is amidated
<220> FEATURE:
<221> NAME/KEY: SITE
<222> LOCATION: 7
<223> OTHER INFORMATION: D-Glu

<400> SEQUENCE: 27

Ser Glu Thr Ser Lys Ser Glu
1               5

<210> SEQ ID NO 28
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..5
<223> OTHER INFORMATION: Cyclic Bridge
<220> FEATURE:
<221> NAME/KEY: SITE
<222> LOCATION: 7
<223> OTHER INFORMATION: Ile at residue 7 is amidated

<400> SEQUENCE: 28

Glu Glu Met Ser Lys Val Ile
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 1..5
<223> OTHER INFORMATION: Cyclic Bridge
<220> FEATURE:
<221> NAME/KEY: SITE
<222> LOCATION: 7
<223> OTHER INFORMATION: Phe at residue 7 is amidated

<400> SEQUENCE: 29
```

```
Glu Asn Thr Ser Lys Ser Phe
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 3..7
<223> OTHER INFORMATION: Cyclic Bridge
<220> FEATURE:
<221> NAME/KEY: SITE
<222> LOCATION: 7
<223> OTHER INFORMATION: Lys at residue 7 is amidated

<400> SEQUENCE: 30

Ser Asn Glu Ser Glu Phe Lys
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 4..8
<223> OTHER INFORMATION: Cyclic Bridge
<220> FEATURE:
<221> NAME/KEY: SITE
<222> LOCATION: 8
<223> OTHER INFORMATION: Lys at residue 8 is amidated

<400> SEQUENCE: 31

Ser Asn Thr Glu Glu Ser Phe Lys
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 3..7
<223> OTHER INFORMATION: Cyclic Bridge
<220> FEATURE:
<221> NAME/KEY: SITE
<222> LOCATION: 7
<223> OTHER INFORMATION: Lys at residue 7 is amidated

<400> SEQUENCE: 32

Lys Asn Thr Ser Glu Ser Phe
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 2..6
<223> OTHER INFORMATION: Cyclic Bridge
<220> FEATURE:
```

```
<221> NAME/KEY: SITE
<222> LOCATION: 7
<223> OTHER INFORMATION: Phe at residue 7 is amidated

<400> SEQUENCE: 33

Ser Lys Thr Ser Ser Glu Phe
1               5

<210> SEQ ID NO 34
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 3..7
<223> OTHER INFORMATION: Cyclic Bridge
<220> FEATURE:
<221> NAME/KEY: SITE
<222> LOCATION: 7
<223> OTHER INFORMATION: Glu at residue 7 is amidated

<400> SEQUENCE: 34

Ser Asn Lys Ser Ser Phe Glu
1               5

<210> SEQ ID NO 35
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 4..8
<223> OTHER INFORMATION: Cyclic Bridge
<220> FEATURE:
<221> NAME/KEY: SITE
<222> LOCATION: 8
<223> OTHER INFORMATION: Glu at residue 8 is amidated

<400> SEQUENCE: 35

Ser Asn Thr Lys Ser Glu Ser Glu
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic Peptide
<220> FEATURE:
<221> NAME/KEY: SITE
<222> LOCATION: 5..9
<223> OTHER INFORMATION: Cyclic Bridge
<220> FEATURE:
<221> NAME/KEY: SITE
<222> LOCATION: 9
<223> OTHER INFORMATION: Lys at residue 8 is amidated

<400> SEQUENCE: 36

Ser Asn Thr Ser Glu Ser Glu Ser Lys
1               5
```

IMMUNOMODULATING CYCLIC COMPOUNDS

This application is a national stage application under 35 U.S.C. 371 of international application PCT/IB2013/000553, filed Mar. 28, 2013, now abandoned, which claims benefit under 35 U.S.C. 119(a) of Indian application 1213/CHE/2012, filed Mar. 29, 2012, now abandoned.

TECHNICAL FIELD

The present invention relates to novel cyclic compounds useful for treatment of disorders via immuno-potentiation comprising inhibition of immunosuppressive signal induced due to PD-1, PD-L1, or PD-L2 and therapies using them.

The invention also relates to pharmaceutical compositions comprising thereof.

BACKGROUND OF THE INVENTION

Immune system possesses the ability to control the homeostasis between the activation and inactivation of lymphocytes through various regulatory mechanisms during and after an immune response. Among these mechanisms, there are mechanisms that specifically modulate the immune response as and when required. Mechanism via PD-1 pathway relates to almost every aspect of immune responses including autoimmunity, tumour immunity, infectious immunity, transplantation immunity, allergy and immunological privilege. PD-1 (or Programmed Cell Death 1 or PDCD1) is a ~55 kD type I membrane glycoprotein and is a receptor of the CD28 superfamily that negatively regulates T cell antigen receptor signalling by interacting with the specific ligands and is suggested to play a role in the maintenance of self tolerance.

The PD-1 protein's structure comprise of an extracellular IgV domain followed by a trans-membrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals. Also, PD-1 is expressed on the surface of activated T cells, B cells, and macrophages, (Y. Agata et al., Int Immunol, May 1996, 8, 765) suggesting that compared to CTLA-4 [(Cytotoxic T-Lymphocyte Antigen 4), also known as CD152 (Cluster of differentiation 152), a protein that also plays an important regulatory role in the immune system], PD-1 more broadly negatively regulates immune responses.

Indeed, functional "exhaustion" (immune dysfunction) among T and B cell subsets is a well-described feature of chronic viral infections, such as hepatitis B and C and HIV viruses. T cell exhaustion was initially described for CD8 T cells in mice chronically infected with lymphocytic choriomeningitis virus clone 13. In the lymphocytic choriomeningitis virus mouse model, repeated antigen stimulation through the T cell antigen receptor drives the sustained expression of T cell inhibitory receptors, including programmed cell death-1 (PD-1) and lymphocyte activation-gene-3 (LAG-3), on virus-specific CD8 T cells (Joseph Illingworth et al., Journal of Immunology (2013), 190(3), 1038-1047).

Blockade of PD-1, an inhibitory receptor expressed by T cells, can overcome immune resistance. PD-1 is a key immune check point receptor expressed by activated T cells, and it mediates immune suppression. PD-1 functions primarily in peripheral tissues, where T cells may encounter the immune suppressive PD-1 ligands; PD-L1 (B7-H1) and PD-L2 (B7-DC), which are expressed by tumor cells, stromal cells, or both. Inhibition of the interaction between PD-1 and PD-L1 can enhance T-cell responses in vitro and mediate preclinical antitumor activity (Suzanne L. Topalian et al., N Engl J. Med. 2012, 366(26): 2443-2454).

PD-1 plays critical roles in the regulation of the immune response to cancer, allergy, and chronic viral infection (Julie R. Brahmer et al., N Engl J. Med. 2012, 366(26): 2455-2465).

Tumour cells and virus (including HCV and HIV) infected cells are known to exploit the PD-1 signalling pathway (to create Immunosuppression) in order to escape immune surveillance by host T cells. It has been reported that the PD-1 gene is one of genes responsible for autoimmune diseases like systemic lupus erythematosus (Prokunina et al., Nature Genetics, 2002, Vol. 32, No. 4, 666-669.).

Several potential immunomodulators of PD-1 have been described. For example International application WO 01/14557, WO 2004/004771, WO 2004/056875, WO 02/079499, WO 03/042402, and WO 2002/086083 report PD-1 or PD-L1 inhibitory antibody or fusion protein.

United State patent application US2011318373 reports peptide and their derivatives derived from PD1 ectodomain capable of inhibiting the programmed cell death 1 (PD1) signalling pathway.

In view of the current ongoing research and disclosures as discussed above, it would thus be desirable to explore further therapeutically usefulness of immunomodulatory compounds as peptides or modified peptides.

The present invention therefore provides novel therapeutically useful immunomodulatory compounds as cyclic peptide and its derivatives.

SUMMARY OF INVENTION

The present invention relates to novel cyclic peptide and its derivatives or a pharmaceutically acceptable salt thereof or a stereoisomer thereof, which are capable of modulating the PD1 signalling pathway.

In one aspect, the present invention provides a cyclic peptide compound of formula (I).

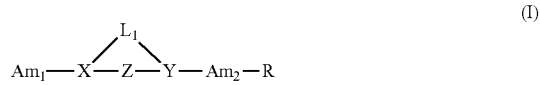

wherein,
$Am_1$ represents 1 to 4 amino acid residues which may be same or different and each independently selected from Ser, Val, Glu, Ile, Asn and Thr; or may be absent;
X is selected from Lys, Glu or Ser;
Y is Glu, Gln or Lys;
$L_1$ represents —CO—$(CH_2)_n$—NH—, —NH—$(CH_2)_n$—CO— or an amide bond between X and Y;
'n' is an integer selected from 1 to 5, both inclusive;
$Am_2$ represents 1 to 3 amino acid residues which may be same or different and each independently selected from Phe, Ser, Glu, Ile, Val, Gln, Tyr and Lys, or may be absent;
Z is $Am_3$-$L_2$;
$L_2$ is —NH—$(CH_2)_n$—CO— or is absent;
$Am_3$ represents 2 to 6 amino acid residues which may be same or different and each independently selected from Thr, Ser, Met, Glu, Asn, Phe and Lys;

R is an amidation of a C-terminal carboxylic acid moiety or is absent;
or a pharmaceutical salt of a peptide derivative of formula (I), or a stereoisomer of a peptide derivative of formula (I) or pharmaceutical salt thereof.

It should be understood that the formula (I) structurally encompasses all stereoisomers, enantiomers and diastereomers, and pharmaceutically acceptable salts that may be contemplated from the chemical structure of the genera described herein.

In another aspect of the present invention, it provides compound of Formula I therapeutically useful in the treatment or prevention of disease or disorder, where there is an advantage in modulation of the PD1 signalling pathway.

BRIEF DESCRIPTION OF ACCOMPANYING DRAWINGS

FIG. 1 shows the in vivo efficacy of compound #2 on lung metastasis in a B16F10 subcutaneous melanoma model.

AMINO ACID SEQUENCE INFORMATION

SEQ ID NO: 1 shows the amino acid sequence of the extracellular domain of human PD-1.
SEQ ID NO: 2 shows the amino acid sequence of the BC Loop.

DETAILED DESCRIPTION OF THE INVENTION

The term 'peptide' is used herein to designate a sequence of natural or unnatural amino acids bonded in said sequence by peptide bonds.

The term "peptide bond" as used herein refers to the chemical bond between carbon and nitrogen in the bivalent group CONH that unites amino acid residues in a peptide.

The term 'compound(s)' as used herein comprises peptides and modified peptides as disclosed in the present invention.

The following common abbreviations of the amino acids are used throughout this specification:

| | | |
|---|---|---|
| Gly (or G)—glycine | Ala (or A)—alanine | Val (or V)—valine |
| Leu (or L)—leucine | Ile (or I)—isoleucine | Orn—ornithine |
| Pro (or P)—proline | Phe (or F)—phenylalanine | Trp (or W)—tryptophan |
| Met (or M)—methionine | Ser (or S)—serine | Thr (or T)—threonine |
| Cys (or C)—cysteine | Tyr (or Y)—tyrosine | Asn (or N)—asparagine |
| Gln (or Q)—glutamine | Asp (or D)—aspartic acid | Glu (or E)—glutamic acid |
| Lys (or K)—lysine | Arg (or R)—arginine | His (or H)—histidine |

Modifications of the peptides discussed hereinafter and wherever relevant may include replacements of some of the L-amino acids by D-amino acids, bonding of amino acids at other than alpha amino groups, including at side chain amino or carboxylic groups, inclusion of non-peptide linkers between peptide sequences, lipidation, and PEGylation.

The present invention provides immunosuppression modulating peptides capable of modulating the PD1 signalling pathway.

In our endeavour to provide novel immunomodulatory compounds, the first embodiment of the present invention provides the structure of compounds as set forth in formula (I)

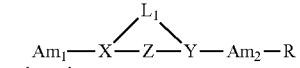

wherein,
$Am_1$ represents 1 to 4 amino acid residues which may be same or different and each independently selected from Ser, Val, Glu, Ile, Asn and Thr; or may be absent;
X is selected from Lys, Glu or Ser;
Y is Glu, Gln or Lys;
$L_1$ represents —CO—$(CH_2)_n$—NH—, —NH—$(CH_2)_n$—CO— or an amide bond between X and Y;
'n' is an integer selected from 1 to 5, both inclusive;
$Am_2$ represents 1 to 3 amino acid residues which may be same or different and each independently selected from Phe, Ser, Glu, Ile, Val, Gln, Tyr and Lys, or may be absent;
Z is $Am_3$-$L_2$;
$L_2$ is —NH—$(CH_2)_n$—CO— or is absent;
$Am_3$ represents 2 to 6 amino acid residues which may be same or different and each independently selected from Thr, Ser, Met, Glu, Asn, Phe and Lys;
R is an amidation of a C-terminal carboxylic acid moiety or is absent;
or a pharmaceutical salt of a peptide derivative of formula (I), or a stereoisomer of a peptide derivative of formula (I) or pharmaceutical salt thereof.

In another embodiment of the present invention, it provides the structure of compounds as set forth in formula (Ia)

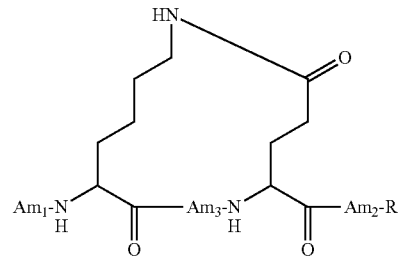

wherein,
$Am_1$, $Am_2$, $Am_3$ and R are same as defined in formula (I);
or a pharmaceutical salt of a peptide derivative of formula (Ia), or a stereoisomer of a peptide derivative of formula (Ia) or pharmaceutical salt thereof.

In yet another embodiment of the present invention, it provides the structure of compounds as set forth in formula (Ib). h

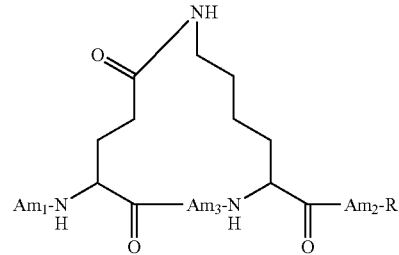

wherein, $Am_1$, $Am_2$, $Am_3$ and R are same as defined in formula (I);

or a pharmaceutical salt of a peptide derivative of formula (Ib), or a stereoisomer of a peptide derivative of formula (Ib) or pharmaceutical salt thereof.

In yet another embodiment of the present invention, it provides the structure of compounds as set forth in formula (Ic)

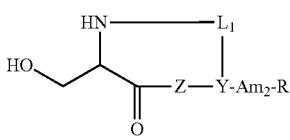

(Ic)

wherein,

Z is as defined in formula (I);

Y is Glu or Gln;

$L_1$ is —CO—$(CH_2)_n$—NH— or an amide bond;

'n' is an integer selected from 2 to 5, both inclusive;

R is an amidation of a C-terminal carboxylic acid moiety or is absent;

or a pharmaceutical salt of a peptide derivative of formula (Ic), or a stereoisomer of a peptide derivative of formula (Ic) or pharmaceutical salt thereof.

The embodiment below are illustrative of the present invention and are not intended to limit the claims to the specific embodiments exemplified.

In one embodiment, specifically provided are compounds of the formula (Ia) in which $Am_1$ is Ser, Ser-Asn, Ser-Asn-Thr or absent.

In another embodiment, specifically provided are compounds of the formula (Ia) in which $Am_2$ is Ser-Phe, Phe or absent.

In yet another embodiment, specifically provided are compounds of the formula (Ia) in which $Am_3$ is Thr-Ser, Asn-Thr-Ser, Thr-Ser-Ser, Ser-Ser-Phe or Ser-Glu-Ser.

In yet another embodiment, specifically provided are compounds of the formula (Ia) in which $Am_1$ is Ser; $Am_3$ is Thr-Ser or Thr-Ser-Ser; $Am_2$ is Ser-Phe or Phe and R is an amidation of a C-terminal carboxylic acid moiety.

In yet another embodiment, specifically provided are compounds of the formula (Ia) in which $Am_1$ is absent; $Am_3$ is Asn-Thr-Ser; $Am_2$ is Ser-Phe and R is an amidation of a C-terminal carboxylic acid moiety.

In yet another embodiment, specifically provided are compounds of the formula (Ib) in which $Am_1$ is Ser, Ser-Asn-Thr-Ser, Glu, Ile, Val, Ser-Asn, Ser-Asn-Thr or absent.

In yet another embodiment, specifically provided are compounds of the formula (Ib) in which $Am_2$ is Ser-Phe, Ser-Ile, Val-Phe, Ser-Val, Ile-Phe, Ser-Gln, Val-Gln, Ser-Tyr, Phe, Ser-D-Glu, Val-Ile, Ser-Phe-Lys or absent.

In yet another embodiment, specifically provided are compounds of the formula (Ib) in which $Am_3$ is Thr-Ser, Ser-Glu-Ser, Met-Ser, Thr-Ser-Ser, Asn-Thr-Ser, Ser-Ser-Phe or Glu-Ser-Phe.

In yet another embodiment, specifically provided are compounds of the formula (Ib) in which R is amidation of a C-terminal carboxylic acid moiety or is absent.

In yet another embodiment, specifically provided are compounds of the formula (Ib) in which $Am_1$ is Ser; $Am_3$ is Thr-Ser, Met-Ser or Thr-Ser-Ser; $Am_2$ is Ser-Phe, Ser-Ile, Val-Phe, Ser-Val, Ile-Phe, Ser-Tyr, Phe, Ser-DGlu or Ser-Phe-Lys and R is an amidation of a C-terminal carboxylic acid moiety or is absent.

In yet another embodiment, specifically provided are compounds of the formula (Ib) in which $Am_1$ is Ser-Asn-Thr-Ser; $Am_3$ is Ser-Glu-Ser; $Am_2$ is a bond and R is an amidation of a C-terminal carboxylic acid moiety.

In yet another embodiment, specifically provided are compounds of the formula (Ib) in which $Am_1$ is Glu; $Am_3$ is Thr-Ser or Met-Ser; $Am_2$ is Ser-Phe or Val-Ile and R is an amidation of a C-terminal carboxylic acid moiety.

In yet another embodiment, specifically provided are compounds of the formula (Ib) in which $Am_1$ is Ile; $Am_3$ is Thr-Ser or Met-Ser; $Am_2$ is Ser-Phe, Ser-Gln or Val-Gln and R is absent.

In yet another embodiment, specifically provided are compounds of the formula (Ic) in which Z is $Am_3$-$L_2$ wherein $Am_3$ is Asn-Thr-Ser-Glu-Ser-Phe, Glu-Thr-Ser-Lys-Ser-Phe or Asn-Thr-Ser and $L_2$ is absent.

In yet another embodiment, specifically provided are compounds of the formula (Ic) in which Z is $Am_3$-$L_2$ wherein $Am_3$ is Asn-Thr-Ser-Glu-Ser-Phe and $L_2$ is —NH—$(CH_2)_5$—CO—.

In yet another embodiment, specifically provided are compounds of the formula (Ic) in which $L_1$ is an amide bond.

In yet another embodiment, specifically provided are compounds of the formula (Ic) in which $L_1$ is —CO—$(CH_2)_5$—NH—.

In yet another embodiment, specifically provided are compounds of the formula (Ic) in which R is an amidation of a C-terminal carboxylic acid moiety.

In yet another embodiment, specifically provided are compounds of the formula (Ic) in which R is absent.

In yet another embodiment, specifically provided are compounds of the formula (Ic) in which Y is Gln; Z is $Am_3$-$L_2$ wherein $Am_3$ is Asn-Thr-Ser-Glu-Ser-Phe or Glu-Thr-Ser-Lys-Ser-Phe and $L_2$ is —NH—$(CH_2)_5$—CO— or is absent; and R is absent.

In yet another embodiment, specifically provided are compounds of the formula (Ic) in which Y is Glu; Z is $Am_3$-$L_2$ wherein $Am_3$ is Asn-Thr-Ser-Glu-Ser-Phe or Glu-Thr-Ser-Lys-Ser-Phe and $L_2$ is absent; and R is an amidation of a C-terminal carboxylic acid moiety.

In yet another embodiment, specifically provided are compounds of the formula (I) in which $Am_1$ represents 1 to 4 amino acid residues which may be same or different and each independently selected from Ser, Val, Glu, Ile, Asn and Thr or absent; X is selected from Lys, Glu or Ser; with the proviso that when X is Ser then $Am_1$ is absent; Y is Glu or Lys; $L_1$ is —CO—$(CH_2)_n$—NH—, —NH—$(CH_2)_n$—CO— or an amide bond, which form a cyclic structure together with free carboxylic acid and amino group of X and Y; 'n' is an integer selected from 1 to 5, both inclusive; $Am_2$ represents direct bond or 1 to 2 amino acid residues which may be same or different and each independently selected from Phe, Ser, Glu, Ile, Val, Gln and Tyr; Z is $Am_3$-$L_2$; $L_2$ is —NH—$(CH_2)_n$—CO— or absent; $Am_3$ represents 2 to 6 amino acid residues which may be same or different and each independently selected from Thr, Ser, Met, Glu, Asn, Phe and Lys; R is free C-terminal, amidated C-terminal or amidated gamma C-terminal.

In an embodiment, specific compounds of formula (I) without any limitation are enumerated in Table (1):

TABLE 1
| Compound No | Structure |
|---|---|
| 1 | 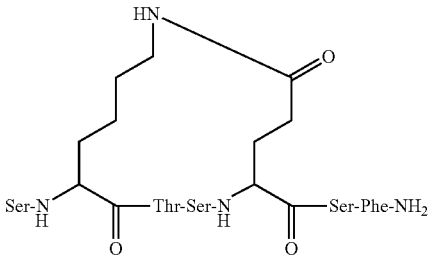<br>(SEQ ID NO: 3) |
| 2 | 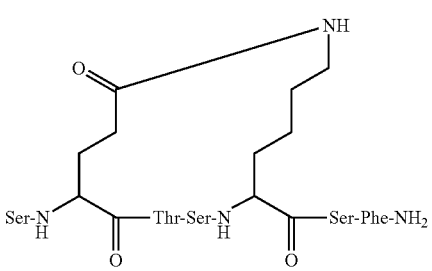<br>(SEQ ID NO: 4) |
| 3 | 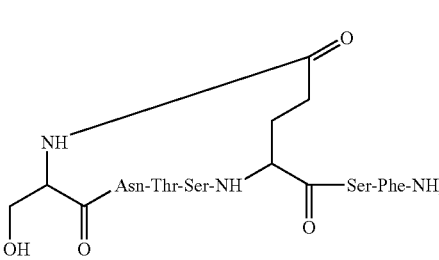<br>(SEQ ID NO: 5) |
| 4 | 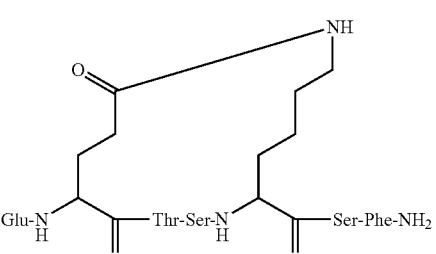<br>(SEQ ID NO: 6) |
| 5 | 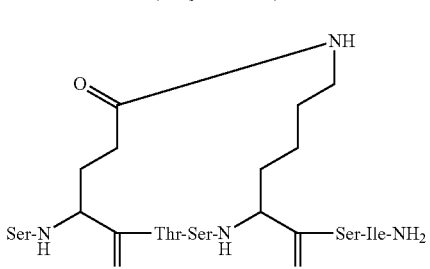<br>(SEQ ID NO: 7) |

TABLE 1-continued
| Compound No | Structure |
|---|---|
| 6 | 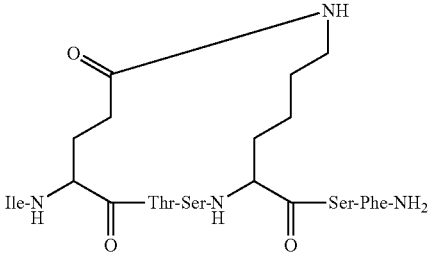(SEQ ID NO: 8) |
| 7 | 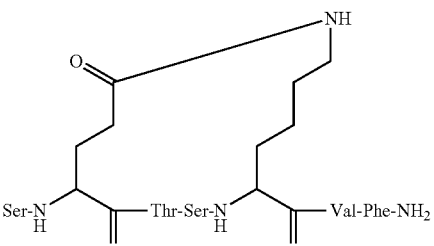(SEQ ID NO: 9) |
| 8 | 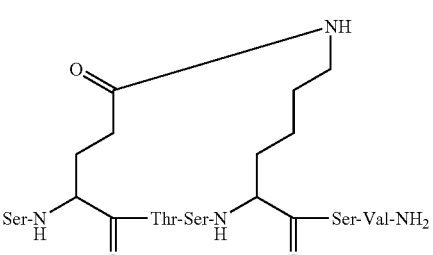(SEQ ID NO: 10) |
| 9 | 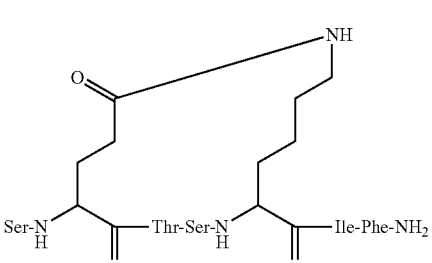(SEQ ID NO: 11) |
| 10 | 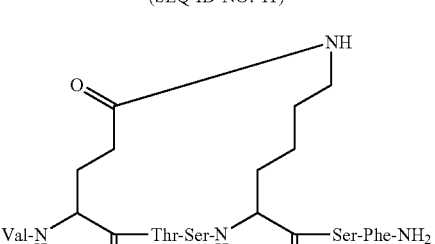(SEQ ID NO: 12) |

TABLE 1-continued
| Compound No | Structure |
|---|---|
| 11 | 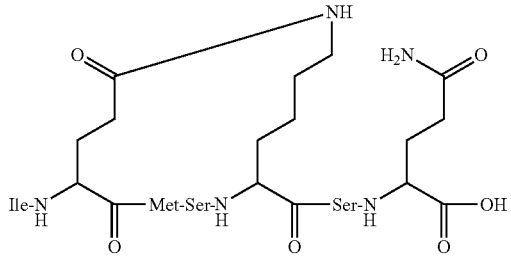<br>(SEQ ID NO: 13) |
| 12 | 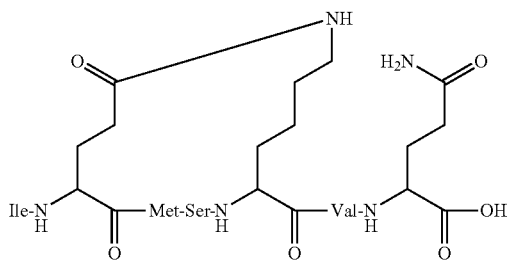<br>(SEQ ID NO: 14) |
| 13 | 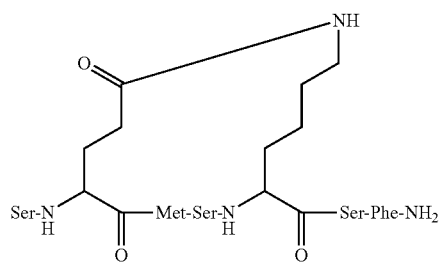<br>(SEQ ID NO: 15) |
| 14 | 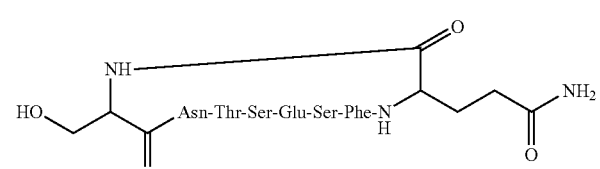<br>(SEQ ID NO: 16) |
| 15 | 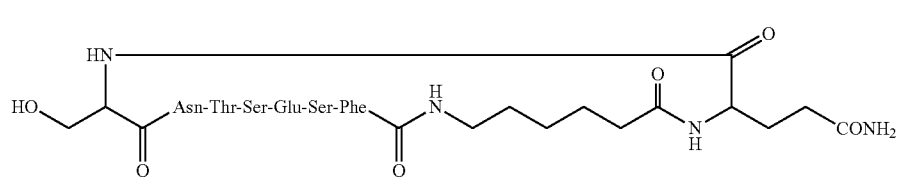<br>(SEQ ID NO: 17) |

TABLE 1-continued

| Compound No | Structure |
|---|---|
| 16 | Ser(HO-)-[cyclic via HN to C=O]-Glu-Thr-Ser-Lys-Ser-Phe-NH-CH(CONH₂ sidechain)-C(=O)NH₂ (SEQ ID NO: 18) |
| 17 | Ser(HO-)-NH-C(=O)-(CH₂)₅-NH-C(=O)-Glu-Thr-Ser-Lys-Ser-Phe-NH-CH(CH₂CH₂CONH₂)-C(=O)NH₂ (SEQ ID NO: 19) |
| 18 | Ser(HO-)-NH-C(=O)-(CH₂)₅-NH-C(=O)-Asn-Thr-Ser-Glu-Ser-Phe-NH-CH(CH₂CH₂CONH₂)-C(=O)NH₂ (SEQ ID NO: 20) |
| 19 | Ser(HO-)-NH-C(=O)-(CH₂)₅-NH-C(=O)-Asn-Thr-Ser-Glu-Ser-Phe-NH-CH(CONH₂)-CONH₂ (SEQ ID NO: 21) |
| 20 | Ser(HO-)-[cyclic via HN to C=O]-Glu-Thr-Ser-Lys-Ser-Phe-NH-CH(-)-C(=O)NH₂ (SEQ ID NO: 22) |
| 21 | Ser-NH-CH(sidechain C(=O)-cyclic-NH)-C(=O)-Thr-Ser-NH-CH(sidechain (CH₂)₄-NH-cyclic)-C(=O)-Ser-Tyr-NH₂ (SEQ ID NO: 23) |

TABLE 1-continued
| Compound No | Structure |
|---|---|
| 22 | 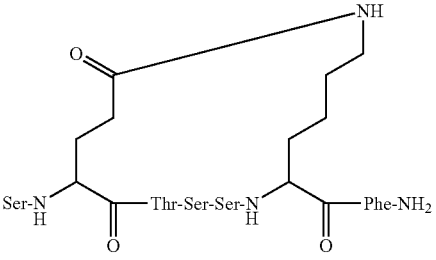<br>(SEQ ID NO: 24) |
| 23 | 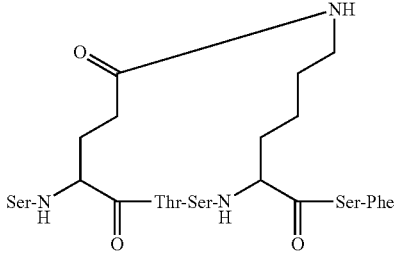<br>(SEQ ID NO: 25) |
| 24 | 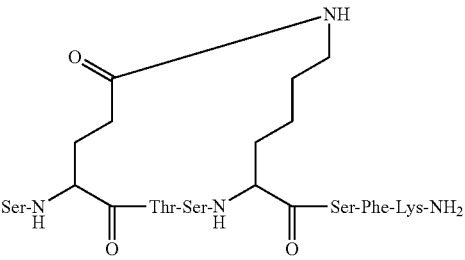<br>(SEQ ID NO: 26) |
| 25 | 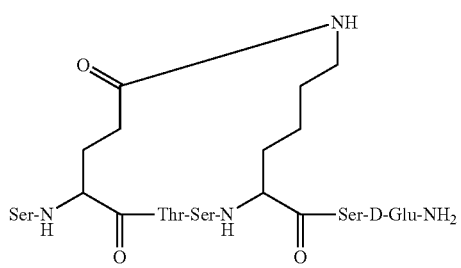<br>SE*TSK*SE {C-terminus Glutamic acid is D-Glu}<br>(SEQ ID NO: 27) |
| 26 | 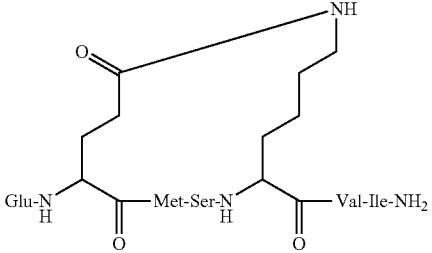<br>(SEQ ID NO: 28) |

TABLE 1-continued

| Compound No | Structure |
|---|---|
| 27 | H₂N–[Glu(side chain C(=O)–NH–(CH₂)₄–Lys)]–Asn-Thr-Ser-NH–[Lys]–Ser-Phe-NH₂ (cyclized via Glu side chain to Lys side chain)<br>(SEQ ID NO: 29) |
| 28 | Ser-Asn-NH–[Glu]–Ser-Ser-Phe-NH–[Lys]–NH₂ (cyclized via Glu side chain to Lys side chain)<br>(SEQ ID NO: 30) |
| 29 | Ser-Asn-Thr-NH–[Glu]–Glu-Ser-Phe-NH–[Lys]–NH₂ (cyclized via Glu side chain to Lys side chain)<br>(SEQ ID NO: 31) |
| 30 | H₂N–[Lys]–Asn-Thr-Ser-NH–[Glu]–Ser-Phe-NH₂ (cyclized via Lys side chain to Glu side chain)<br>(SEQ ID NO: 32) |
| 31 | Ser-NH–[Lys]–Thr-Ser-Ser-NH–[Glu]–Phe-NH₂ (cyclized via Lys side chain to Glu side chain)<br>(SEQ ID NO: 33) |

TABLE 1-continued

| Compound No | Structure |
|---|---|
| 32 | 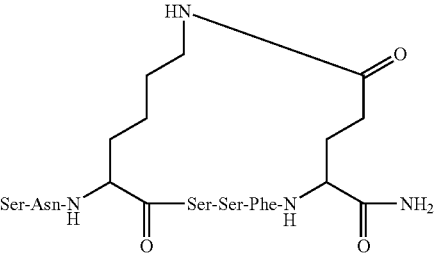<br>(SEQ ID NO: 34) |
| 33 | 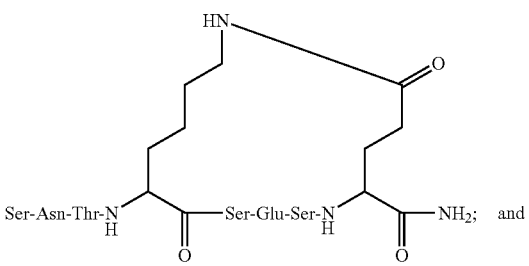<br>(SEQ ID NO: 35) |
| 34 | 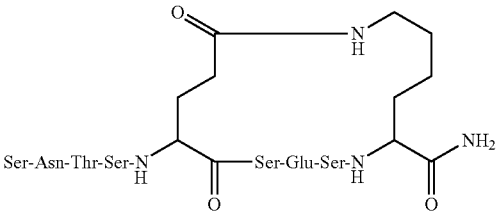<br>(SEQ ID NO: 36) |

The present invention further provides modifications, derivatives of the peptides and pharmaceutical compositions comprising the peptides for treatment of cancer or infection via immunopotentiation caused by inhibition of immunosuppressive signal induced by PD-1, PD-L1, or PD-L2 and therapies using them, immunopotentiative substrates included as the active ingredients.

In accordance with the present invention, in one of the embodiment there are provided compounds capable of inhibiting ability to inhibit the programmed cell death 1 (PD1) signalling pathway and being capable of reducing PD-L1 or PD-L2 binding to PD-1 and resulting immunosuppressive signalling by PD-1, wherein the compound comprises a peptide moiety or a modified peptide moiety derived from the peptide fragments of PD1 peptide itself.

The complete amino acid sequence of human PD-1 is disclosed in U.S. Pat. No. 5,629,204 (Honjo et. al.) and Finger et al., (Gene, 1997, 197, 177-187). Human and mouse PD-1 share around 60% amino acid identity, whereas the extracellular IgV domain shows only 21% and 16% sequence identity with CD28 and CTLA4, respectively.

PD-1 possesses an ectodomain having multiple loop structures and strands between the loops. The amino acid sequence of the extracellular domain of human PD-1 is as set forth in SEQ ID NO: 1.

Extracellular domain of human PD-1
SEQ ID NO: 1
PPTFSPALLVVTEGDNATFTCSFSNTSESFVLNWYRMSPSNQTDKLAAF

PEDRSQPGQDCRFRVTQLPNGRDFHMSVVRARRNDSGTYLCGAISLAPK

AQIKESLRAELRVTERRAEVPTAHPSPSPRSAGQFQTLV

These loop and strand assignments of amino acids are based on the 1.8-Å-resolution structure of the murine PD-1/PD-L2 complex reported in Lazar-Molnar et al, (PNAS, 2008, 105, 30, 10483-10488).

Out of the various loops and strands of the PD-1 ectodomain, BC loop (i.e. $24^{th}$ to $30^{th}$ amino acid of SEQ ID NO: 1) was taken up for further modification. The present invention provides compounds comprising of modified BC loop of extracellular domain of human PD-1.

SEQ ID NO: 2 BC Loop comprised of amino acid sequence as

SNTSESF.

Compounds of the invention may comprise peptide moieties that are lipidated. One or more of the amino acids of the peptide may be a D-amino acid with a view to provide improved stability in vivo.

The invention includes compounds as described above, formulated for pharmaceutical administration, typically by combination with a pharmaceutically acceptable carrier or diluent.

The invention includes compounds as described above for use in a method of medical treatment, e.g. in the treatment of cancer, treatment of bacterial and viral infections.

The invention further includes a method of screening compounds for ability to block interaction between PD-1 and a PD-1 ligand, comprising contacting candidate compounds of the kind described above with PD-1 or a PD-1 ligand binding portion of PD-1 and with a PD-1 ligand or a PD-1 binding portion of a PD-1 ligand, and measuring the extent of PD-1/PD-1 ligand binding.

In addition, compounds of the invention may be combined with carrier molecules such as dendrimers, e.g. PAMAM dendrimers, liposomes, micro-particles and nano-particles such as polycyanoacrylate nanoparticles, and these also may be PEGylated.

In one of the embodiment of the present invention there is provided a compound having the ability to inhibit the programmed cell death 1 (PD1) signalling pathway and being capable of reducing PD-L1 or PD-L2 binding to PD-1 and resulting immunosuppressive signalling by PD-1.

Further embodiment of the present invention relates to the compounds as disclosed in the present invention, wherein one or more of the amino acids of the peptide moiety the compounds is substituted with a D-amino acid.

The compounds as disclosed in the present invention are formulated for pharmaceutical administration.

Another embodiment of the present invention provided a pharmaceutical composition comprising the compound as disclosed, and a pharmaceutically acceptable carrier or diluent.

Yet another embodiment of the present invention provides use of the compounds as disclosed in the present invention for the preparation of a medicament for the treatment of cancer.

Yet another embodiment of the present invention provides use of the compounds as disclosed in the present invention for the preparation of a medicament for the treatment of bacterial and viral infection.

Yet another embodiment of the present invention provides a method of treatment of cancer, wherein the method comprises administration of an effective amount of the compound and/or peptides of the present invention to the subject in need thereof.

Yet another embodiment of the present invention provides a method for inhibiting growth of tumour cells and/or metastasis by administering an effective amount of the compound of the present invention to the subject in need thereof.

The said tumour cells include cancer such as but not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

Still yet another embodiment of the present invention provides a method of treatment of infection via immunopotentiation caused by inhibition of immunosuppressive signal induced by PD-1, PD-L1, or PD-L2, wherein the method comprises administration of an effective amount of the compound and/or peptides of the present invention to the subject in need thereof.

The infectious disease includes but not limited to HIV, Influenza, Herpes, *Giardia, Malaria, Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

The compounds of the present invention may be used as single drugs or as a pharmaceutical composition in which the compound is mixed with various pharmacologically acceptable materials.

The pharmaceutical composition is usually administered by a parenteral administration route, but can be administered by oral or inhalation routes. Examples of the parenteral administration include administration by injection, and percutaneous, transmucosal, transnasal and trans pulmonary administrations.

The injectable materials include a solution, a suspension, and a solid injection that is dissolved or suspended in a solvent before use.

The injection is used after one or more active ingredients are dissolved, suspended or emulsified in a solvent. Examples of the solvent include water-soluble solvents (e.g., distilled water, physiological saline and Ringer's solution), oil solvents (e.g., vegetable oils such as olive oil, sesame oil, cotton oil and corn oil, and alcohols such as propylene glycol, polyethylene glycol and ethanol), and combinations thereof.

Further, the injection may contain a stabilizer (e.g., human serum albumin), solubilizing agent (e.g., polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate), suspending agent (e.g., surfactants such as stearyl triethanolamine, sodium lauryl sulfate, lauryl aminopropionic acid, lecithin, benzalkonium chloride, benzethonium chloride and glyceryl monostearate; hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose; polysorbates; and polyoxyethylene hardened castor oil), emulsifier, soothing agent (e.g., benzyl alcohol), tonicity agent (e.g., sodium chloride, glycerin, D-mannitol, D-sorbitol and glucose), buffer, preservative (e.g., methylparaben, propylparaben, benzyl alcohol, chlorobutanol and phenol), antiseptic (e.g., paraoxybenzoic esters, chlorobutanol, benzyl alcohol, phenethyl alcohol, dehydroacetic acid and sorbic acid), antioxidant (e.g., sulfite and ascorbate) and dispersant (e.g., Polysorbate 80, Polyoxyethylene hardened castor oil 60, ethylene glycol, carboxymethyl cellulose and sodium alginate).

These injections may be prepared by known methods in the formulation technology field, such as by a method described in various Pharmacopoeia. They are prepared, for example, through a sterilization process at the final stage, or by aseptic manipulation. It is also possible to use an aseptic solid formulation, such as a freeze dried product, wherein the aseptic solid formulation is prepared and dissolved in aseptic or sterilized distilled water for injection or other solvents before use.

These parenteral solutions may be supplied in a vessel with a standard capacity, such as a plastic or glass vial, ampoule, syringe and injector, or in a vessel with a large capacity, such as a bottle.

The dosage of the compounds of the present invention varies depending on age, weight, symptom, therapeutic efficacy, dosing regimen and/or treatment time. Generally, they may be administered by a parenteral route (preferably intravenous administration) in an amount of 1 mg to 100 mg per time, from once a couple of days, once 3 days, once 2 days, once a day to a couple of times a day, in the case of an adult, or continuously administered by intravenous administration from 1 to 24 hours a day. Since the dosage is affected by various conditions, an amount less than the above dosage may sometimes work well enough, or higher dosage may be required in some cases.

Parenteral administration by injection includes all forms of injections, and also includes intravenous fluids. For example, it includes intramuscular injections, subcutaneous injections, intradermal injections, intraarterial injections, intravenous injections, intraperitoneal injections, injections to spinal cavity, and intravenous drops.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the peptide of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

Particularly, since the compound of the present invention exhibits an effect of stimulating or proliferating lymphoid cells, the concomitant use is able to reduce a dosage of chemotherapeutics commonly used or an irradiation dosage in radio therapy. This results in suppression of side effects that accompany with chemotherapy and radio therapy.

The compound of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutrophenia) treatment drug, thrombocytopenia treatment drug, antiemetic and cancer pain intervention drug, concomitantly or in a mixture form.

The compound of the present invention can be used with other immunomodulators concomitantly or in a mixture form. Examples of the immunomodulator include various cytokines Examples of the cytokines that stimulates immune responses include GM-CSF, M-CSF, G-CSF, interferon-α, β, or γ, IL-1, IL-2, IL-3 and IL-12.

The concomitant use of the compound of the present invention and a cancer antigen is able to give an additive or synergetic enhancement effect. Examples of the cancer antigen include HLA-A1 and HLA-A2 derived peptides derived from MAGE-1 or MAGE-3 of malignant melanoma, MART-1 and gp100, HER2/neu peptide of breast cancer and ovarian cancer, MUC-1 peptide of adenocarcinoma and NY-ESO-1 of metastatic cancer.

EXPERIMENTAL

Different immunomodulatory compounds of the present invention were prepared via solid phase peptide synthesis, which was carried out manually using either a custom made glass reactor with a frit or polyethylene vessel equipped with a polypropylene filter.

All the compounds described herein, including compounds of general formula (I), (Ia) (Ib) and (Ic), and specific examples are prepared using techniques known to one skilled in the art through the procedure depicted below or by other methods. Furthermore, in the following procedures, where specific acids, bases, reagents, coupling agents, solvents, etc. are mentioned, it is understood that other suitable acids, bases, reagents, coupling agents etc. may be used and are included within the scope of the present invention. The compounds obtained by using the below procedures may be of insufficient purity. These compounds can be purified by using any of the methods for purification of organic compounds known to persons skilled in the art, for example, crystallization or silica gel or alumina column chromatography using different solvents in suitable ratios. All possible stereoisomers are envisioned within the scope of this invention.

Removal of Allyloxycarbonyl (Alloc)/OAll Group of Side Chain of Lysine and Glutamic Acid After the completion of the linear protected peptide sequence, the Alloc-protecting group from Lys (Alloc) and allyl protecting group from Glutamic acid was removed from the peptidyl resin by treating with tetrakistriphenylphosphine palladium (0) (10 Equiv) and Phenyl silane (20 eqv) in a solution of chloroform/N-methylpyrrolidine (95/5 v/v) for 6 h under argon. The resin (1 g) was washed with a solution of 10% NMP in chloroform (6×15 m L); 1% DIEPA in DMF (6×15 m L); DCM (6×15 m L); DMF (6×15 m L); and finally with NMP (3×15 ml each); The deprotection and resulting free amino group was confirmed by Kaiser test.

Lactam bridge/Cyclisation:

A solution of HOBT/DIC (5 equivalent each relative to resin loading) in NMP was added to the resin and coupling was carried out overnight. After 18 hr the resin was filtered and washed with DMF/DCM/DMF (6×10 m L). Kaiser test was carried out and in case of slight blue colouration, the peptidyl resin was capped with acetylating mixture (Pyridine/DCM/acetic anhydride: 8:8:1). After 30 min, the resin was filtered and washed with DMF/DCM/DMF (6×10 m L each)

Procedure for Cleavage of Peptidyl Resin and Global Deprotection

The peptidyl Resin was washed with MeOH (6×15 ml) and solvent ether (3×15 ml) and dried under vacuum. The cleavage of the peptides from the solid support is achieved by treating the peptide-resin with cleavage cocktail as specified for each peptide at room temperature for 2.5 h. Cleavage mixture was collected by filtration and the resin was washed with TFA and DCM. The excess TFA and DCM was concentrated to small volume under nitrogen and DCM was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged and the supernatant ether was removed and fresh ether was added to the peptide and re-centrifuged. The residue was dissolved in Millipore water and lyophilized to obtain the crude peptide.

Cleavage cocktail A=80% TFA/5% phenol/5% thioanisole/2.5% 1,2 ethanedithiol/5% DCM/2.5% DMS Cleavage Cocktail B=90% TFA/5% TIPS/5% water Purification and Characterization of Peptide The Reverse phase analytical HPLC was performed using on Zorbax Eclipse XDB-C18 silica column (4.6 mm×250 mm, 5 μm).

The elution conditions used are

Method-1: Buffer A: 0.1% TFA/Water, Buffer B: 0.1% TFA in 9:1 acetonitrile/water.

Equilibration of the column with 2% buffer B and elution by a gradient of 2% to 70% buffer B during 15 min.

LCMS was performed on AP1 2000 LC/MS/MS triple quad (Applied biosystems) with Agilent 1100 series HPLC with G1315 B diode array detector (DAD) or using Agilent LC/MSD VL single quad with Agilent 1100 series HPLC with G1315 B DAD.

For further illustration of methods of preparing the compounds of the present invention, the following examples are disclosed below.

Example: 1

Synthesis of Compound 2 (SEQ ID NO: 4)

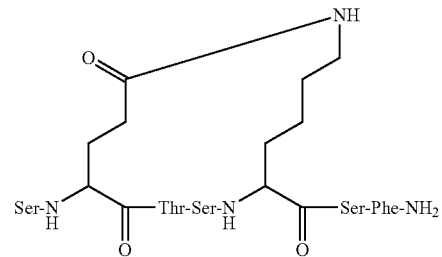

Desiccated Rink Amide MBHA-Amide resin (100-200 mesh, 0.66 mmol/g, 2 g) was placed in a polyethylene vessel equipped with a polypropylene filter. Resin was swelled in DCM (25 m L) for 1 h and DMF (25 m L) for 1 h. The Fmoc group of the Rink Amide MBHA-Amide was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deportation was positive. The C-terminal amino acid, Fmoc-Phe-OH (2.6 g; 5 equiv; 6.6 mmol) in dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. After the first amino acid attachment, the unreacted amino group, if any, in the resin is capped, used acetic anhydride/pyridine/DCM (1:8:8) for 20 minutes to avoid any deletion of the sequence. After capping, resin is washed with DCM (6×15 m L), DMF (6×15 m L), DCM (6×15 m L) and DMF (6×15 m L). The Fmoc group on the C-terminal amino acid attached peptidyl resin was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deprotection was positive. Fmoc-Ser (tBu)-OH (2.5 g; equiv; 6.6 mmol) in dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. The Fmoc group of the peptidyl resin was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deprotection was positive. Next amino acid in the peptide sequence Fmoc-Lys(Alloc)-OH (2.9 g; 5 equiv; 6.6 mmol) in dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. On completion of threonine coupling Fmoc group on the peptidyl resin was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deportation was positive. Next amino acid Fmoc-Ser (tBu)-OH (2.5 g; 5 equiv; 6.6 mmol) in dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. The Fmoc group on the peptidyl resin was deprotected by treating it twice with 20% (v/v) piperidine/DMF solution for 5 and 15 min (20 mL). The resin was washed with DMF (6×15 m L), DCM (6×15 m L) and DMF (6×15 m L). Kaiser test on peptide resin aliquot upon completion of Fmoc-deprotection was positive. Fmoc-Thr-(tBu)-OH (2.6 g; 5 equiv; 6.6 mmol) in Dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. The Fmoc group of the peptidyl resin was deprotected by treating it twice with 20% (v/v) piperidine/DMF solution for 5 and 15 min (20 mL). The resin was washed with DMF (6×15 m L), DCM (6×15 m L) and DMF (6×15 m L). Kaiser test on peptide resin aliquot upon completion of Fmoc-deprotection was positive. Next amino acid Fmoc-Glu (OAll)-OH (2.8 g; 5 equiv; 6.6 mmol) in dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. The Fmoc group of the peptidyl resin was deprotected by treating it twice with 20% (v/v) piperidine/DMF solution for 5 and 15 min (20 mL). The resin was washed with DMF (6×15 m L), DCM (6×15 m L) and DMF (6×15 m L). Kaiser test on peptide resin aliquot upon completion of Fmoc-deprotection was positive. Next amino acid Fmoc-Ser (tBu)-OH (2.5 g; 5 equiv; 6.6 mmol) in dry DMF was added to the deprotected resin and coupling was initiated with DIC (1.1 m L; 5 equiv) and HOBT (0.84 g; 5 equiv) in DMF. The concentration of each reactant in the reaction mixture was approximately 0.4 M. The mixture was rotated on a rotor at room temperature for 2 h. Resin was filtered and washed with DMF (6×15 m L), DCM (6×15 m L) and DMF (6×15 m L). Kaiser test on peptide resin aliquot upon completion of coupling was negative. After the completion of the linear protected peptide sequence, the Alloc-protecting group from Lys (Alloc) and Allyl protecting group from Glutamic acid was removed as mentioned in the general procedure using tetrakistriphenylphosphine palladium (0) (10 Equiv; 12.6 g) and Phenyl silane (20 eqv; 1.7 m L). The Lactam Bridge was carried out as mentioned in the general procedure using HOBT (0.7 g)/DIC (0.8 m L) method. The peptidyl resin was cleaved as mentioned in procedure for cleavage using cleavage cocktail B to yield (760 mg), 75% yield. The crude material was purified by preparative HPLC on water's X-bridge, C18, 19×150 mm, 5 um column with buffer A: 0.1% TFA/Water, buffer B: 0.1% TFA/CH$_3$CN. The peptide was eluted by gradient elution 0-4 min=5-20% buffer B, 4-6 min=20-33% buffer B with a flow rate of 15 m L/min. HPLC: RT −10.1 min (97.1%); LCMS Calculated Mass: 765.84, Observed Mass: 766.4 [M]$^+$.

Example: 2

Synthesis of Compound 1 (SEQ ID NO: 3)

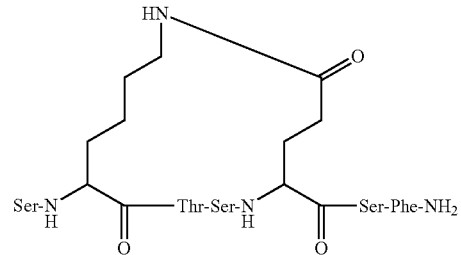

Synthesis was carried out as explained in procedure for compound 2, using Rink Amide MBHA-Amide resin (100-200 mesh, 0.66 mmol/g, 1 g). The C-terminal amino acid was coupled as Fmoc-Phe-OH (1.3 g; 5 equiv) using DIC (0.55 m L; 5 equiv) and HOBT (0.42 g; 5 equiv) in DMF. The remaining amino acids; Fmoc-Ser (OtBu)-OH (1.3 g; 5 equiv), Fmoc-Glu (OAllyl)-OH (1.4 g; 5 equiv), Fmoc-Ser (OtBu)-OH (1.3 g; 5 equiv), Fmoc-Thr-(OtBu)-OH (1.3 g; 5 equiv), Fmoc-Lys(Alloc)-OH (1.5 g; 5 equiv) and Boc-Ser (OtBu)-OH (0.9 g; 5 equiv) were coupled sequentially by following analogous procedure as mentioned in example 1. After the completion of the linear protected peptide sequence, the Alloc-protecting group from Lysine and Allyl protecting group from Glutamic acid was removed as mentioned in the general procedure using tetrakistriphenylphosphine palladium (0) (5 Equiv; 2 g) and Phenyl silane (10 eqv; 0.3 m L). The lactam bridge was carried out as mentioned in the general procedure using HOBT (5 equiv excess)/DIC (5 equiv excess) method. The peptidyl resin was cleaved as mentioned in procedure for cleavage using cleavage cocktail A to yield (380 mg), 75% yield. The crude material was purified by preparative HPLC on Water's X-bridge C18, (19×150 mm, 5um) with buffer A: 0.1% TFA/Water, buffer B: 0.1% TFA/CH₃CN. The peptide was eluted by gradient elution 0-4 min=5-20% buffer B, 4-10 min=20-70% buffer B with a flow rate of 15 mL/min. HPLC: RT –10.3 min (96.5%); LCMS Calculated Mass: 765.84, Observed Mass: 766.3 [M]⁺.

Example: 3

Synthesis of Compound 12 (SEQ ID NO: 14)

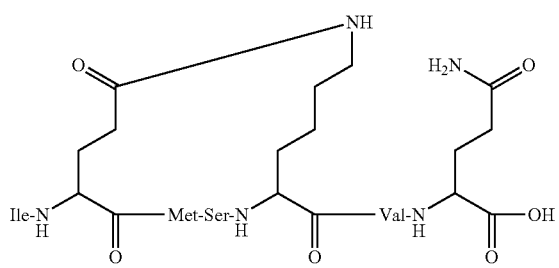

Synthesis was carried out as explained in procedure for compound 2, using Rink Amide MBHA-Amide resin (100-200 mesh, 0.66 mmol/g, 0.5 g). The C-terminal amino acid was coupled as Fmoc-Glu-(OH)-OtBu where γ-carboxyl group of glutamic acid was used as point of attachment and its alpha carboxyl is protected as OtBu ester (0.68 g; 5 equiv; 1.65 mmol) to liberate the free peptide as Gln in the C-terminus. The remaining amino acids; Fmoc-Val (0.6 g), Fmoc-Lys(Alloc)-OH (0.72 g), Fmoc-Ser (tBu)-OH (0.62 g), Fmoc-Met-OH (0.6 g), Fmoc-Glu (OAll)-OH (0.7 g) and Boc-Ile-OH (0.42 g) were coupled sequentially as mentioned in example 1. After the completion of the linear protected peptide sequence, the Alloc-protecting group from Lys (Alloc) and Allyl protecting group from Glutamic acid was removed as mentioned in the general procedure using tetrakistriphenylphosphine palladium (0) (5 Equiv; 2 g) and Phenyl silane (10 eqv; 0.3 m L). The lactam bridge was carried out as mentioned in the general procedure using HOBT (0.18 g)/DIC (0.2 m L) method. The peptidyl resin was cleaved as mentioned in procedure for cleavage using cleavage cocktail A to yield (160 mg), 60% yield. The crude material was purified by preparative HPLC on Phenomex. Luna C18, (10×250 mm, 5 um) with buffer A: 0.1% TFA/Water, buffer B: CH₃CN. The peptide was eluted by gradient elution 0-5 min=10-15% buffer B, 5-25 min=15-25% buffer B with a flow rate of 5 mL/min. HPLC: RT –10.3 min (96.5%); LCMS Calculated Mass: 816.01, Observed Mass: 816.3 [M]⁺.

Example: 4

Synthesis of Compound 14 (SEQ ID NO: 16)

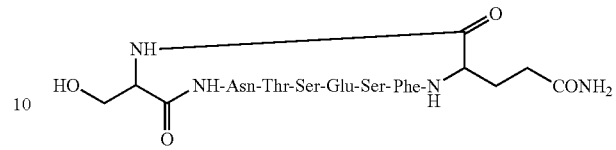

Synthesis was carried out as explained in procedure for compound 2, using Rink Amide MBHA-Amide resin (100-200 mesh, 0.66 mmol/g, 1 g). The C-terminal amino acid was coupled as Fmoc-Glu-(OH)-OAllyl where γ-carboxyl group of Glutamic acid was used as point of attachment and its alpha carboxyl is protected as OAllyl ester (0.92 g; 5 equiv; 3.3 mmol). The remaining amino acids; Fmoc-Phe-OH (0.85 g), Fmoc-Ser (tBu)-OH (0.84 g), Fmoc-Glu (OtBu)-OH (0.94 g), Fmoc-Ser(tBu)-OH (0.84 g), Fmoc-Thr(tBu)-OH (0.87 g), Fmoc-Asn (Trt)-OH (1.3 g) and Fmoc-Ser(tBu)-OH (0.84 g) were coupled sequentially as mentioned in example 1. After the completion of the linear protected peptide sequence with Fmoc, allyl protecting group from the C-terminus was removed as mentioned in the general procedure using tetrakistriphenylphosphine palladium (0) (5 Equiv; 3.8 g) and Phenyl silane (10 eqv; 0.58 m L). The Fmoc group of the N-terminus of the peptidyl resin was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deprotection was positive. Cyclization was carried out as mentioned in the general procedure using HOBT (0.54 g)/DIC (0.82 m L) method. The peptidyl resin was cleaved using cleavage cocktail B to yield (380 mg), 65% yield. The crude material was purified by preparative HPLC on Zorbax Eclipse XDB C18, (9.4×250 mm, 5um) with buffer A: 0.1% TFA/Water, buffer B: CH₃CN. The peptide was eluted by gradient elution 0-2 min=5-10% buffer B, 2-14 min=10-18% buffer B with a flow rate of 7 m L/min. HPLC: RT –10.168 min (96.5%); LCMS Calculated Mass: 880.8, Observed Mass: 881.7 [M+H]⁺.

Example: 5

Synthesis of Compound 15 (SEQ ID NO: 17)

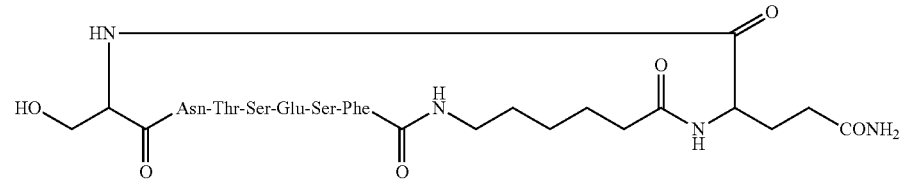

Synthesis was carried out as explained in procedure for compound 2, using Rink Amide MBHA-Amide resin (100-200 mesh, 0.66 mmol/g, 1 g). The C-terminal amino acid was coupled as Fmoc-Glu-(OH)-OAllyl where γ-carboxyl group of Glutamic acid was used as point of attachment and its alpha carboxyl is protected as OAllyl ester (0.92 g; 5 equiv; 3.3 mmol). The remaining amino acids; Fmoc-Ahx-OH (0.82 g), Fmoc-Phe-OH (0.85 g), Fmoc-Ser (tBu)-OH (0.84 g), Fmoc-Glu(OtBu)-OH (0.94 g), Fmoc-Ser(OtBu)-

OH (0.84 g), Fmoc-Thr(OtBut)-OH (0.87 g), Fmoc-Asn (Trt)-OH (1.3 g) and Fmoc-Ser(tBu)-OH (0.84 g) were coupled sequentially as mentioned in example 1. After the completion of the linear protected peptide sequence with Fmoc, allyl protecting group from the C-terminus was removed as mentioned in the general procedure using tetrakistriphenylphosphine palladium (0) (5 Equiv; 3.8 g) and Phenyl silane (10 eqv; 0.58 m L). The Fmoc group of the N-terminus of the peptidyl resin was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deprotection was positive. Cyclization was carried out as mentioned in the general procedure using HOBT (0.54 g)/DIC (0.82 m L) method. The peptidyl resin was cleaved using cleavage cocktail B to yield (680 mg), 70% yield. The crude material was purified by preparative HPLC on Zorbax Eclipse XDB C18, (9.4×250 mm, 5 um) with buffer A: 0.1% TFA/Water, buffer B: CH$_3$CN. The peptide was eluted by gradient elution 0-3 min=10-10% buffer B, 3-60 min=10-50% buffer B with a flow rate of 7 m L/min. HPLC: RT –11.054 min (95.4%); LCMS Calculated Mass: 993.7, Observed Mass: 994.8 [M+H]$^+$.

Example: 6

Synthesis of Compound 17 (SEQ ID NO: 19)

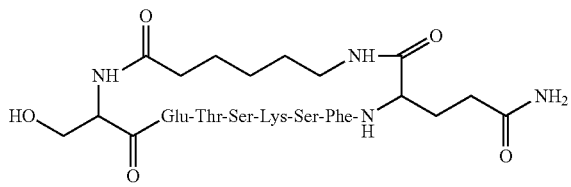

Synthesis was carried out as explained in procedure for compound 2, using Rink Amide MBHA-Amide resin (100-200 mesh, 0.66 mmol/g, 1 g). The C-terminal amino acid was coupled as Fmoc-Glu-(OH)-OAllyl where γ-carboxyl group of gutamic acid was used as point of attachment and its alpha carboxyl is protected as OAllyl ester (0.92 g; 5 equiv; 3.3 mmol). The remaining amino acids; Fmoc-Phe-OH (0.85 g), Fmoc-Ser (tBu)-OH (0.84 g), Fmoc-Lys(Boc)-OH (1.01 g), Fmoc-Ser(tBu)-OH (0.87 g), Fmoc-Thr (tBu)-OH (0.93 g;) and Fmoc-Glu(OtBu)-OH (0.98 g) Fmoc-Ser (tBu)-OH (0.84 g), Fmoc-Ahx-OH (0.82 g), were coupled sequentially as mentioned in example 1. After the completion of the linear protected peptide sequence with Fmoc, allyl protecting group from the C-terminus was removed as mentioned in the general procedure using tetrakistriphenyl-phosphine palladium (0) (5 Equiv; 3.8 g) and Phenyl silane (10 eqv; 0.58 m L). The Fmoc group of the N-terminus of the peptidyl resin was deprotected by treating it twice with 20% (v/v) piperidine/DMF solution for 5 and 15 min (20 m L). The resin was washed with DMF (6×15 m L), DCM (6×15 m L) and DMF (6×15 m L). Kaiser test on peptide resin aliquot upon completion of Fmoc-deprotection was positive. Cyclization was carried out as mentioned in the general procedure using HOBT (0.54 g)/DIC (0.82 m L) method. The peptidyl resin was cleaved using cleavage cocktail B to yield (410 mg), 69% yield. LCMS Calculated Mass: 1007.5, Observed Mass: 1008.6 [M+H]$^+$.

Example: 7

Synthesis of Compound 19 (SEQ ID NO: 21)

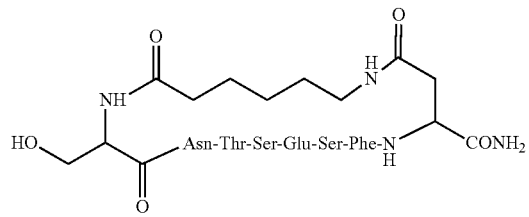

Synthesis was carried out as explained in procedure for compound 2, using Rink Amide MBHA-Amide resin (100-200 mesh, 0.66 mmol/g, 1 g). The C-terminal amino acid was coupled as Fmoc-Glu (OAllyl)-OH (1.3 g; 5 equiv) using DIC (0.52 m L; 5 equiv) and HOBT (0.45 g; 5 equiv) in DMF. The remaining amino acids; Fmoc-Phe-OH (1.25 g; 5 equiv), Fmoc-Ser (OtBu)-OH (1.3 g; 5 equiv), Fmoc-Glu-(OtBu)-OH (1.35 g; 5 equiv.), Fmoc-Ser(OtBu)-OH (1.3 g; 5 equiv), Fmoc-Thr (OtBu)-OH (1.3 g; 5 equiv), Fmoc-Asn (Trt)-OH (1.96 g; 5 equiv), Fmoc-Ser(OtBu)-OH (1.3 g; 5 equiv) and Fmoc-Ahx-OH (1.2 g; 5 equiv) were coupled sequentially as mentioned in example 1. After the completion of the linear protected peptide sequence, allyl protecting group from Glutamic acid was removed as mentioned in the general procedure using tetrakistriphenylphosphine palladium (0) (5 Equiv; 2 g) and Phenyl silane (10 eqv; 0.3 m L). This was followed by Fmoc removal of N-terminal Fmoc protecting group on Ahx using 20% Pip/DMF. Cyclization was carried out as mentioned in the general procedure using HOBT/DIC (both 5 Equiv excess) method. The peptidyl resin was cleaved as mentioned in procedure for cleavage using cleavage cocktail A to yield (400 mg), 60% yield. The crude material was purified by preparative HPLC on Water's X-bridge C18, (9.4×250 mm, Sum) with buffer A: 0.1% TFA/Water, buffer B: 0.1% TFA/CH3CN.; LCMS Calculated Mass: 994.0 Observed Mass: 994.8 [M+H]$^+$.

Example: 8

Synthesis of Compound 23 (SEQ ID NO: 25)

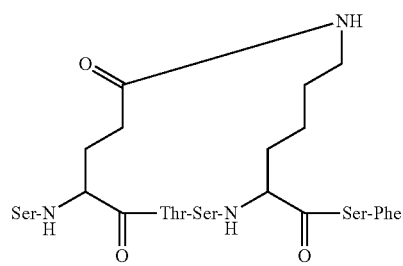

Desiccated 2-chlorotrityl chloride resin (1 g; 1.12 m mol/g) was swelled in DCM for 1 h in a solid phase reaction vessel. Fmoc-Phe-OH (0.53 g, 1.2 equivalents with respect to resin loading) was dissolved in dry DCM was added in to the reaction vessel followed by the addition of 3.8 eq. of DIPEA (0.73 ml). The coupling was carried out at room temperature for 6 h. The resin was filtered and washed with DCM (3×15 mL), DMF (3×15 mL) followed by 1% DIPEA in DMF (3×15 mL). Any unreacted chloride groups were capped using methanol. After 30 min the resin was filtered and washed with diethyl ether, desiccated under vacuum overnight. The Phenylalanine first attached resin was used for further chain elongation and peptide synthesis was carried out as mentioned in example 1.

The other compounds of the Table 1 were prepared by following similar procedure as described above with suitable modification known to the one ordinary skilled in the art. The identity of peptide was confirmed by LCMS (Table 2).

TABLE 2

LCMS characterization

| Comp No | LCMS | |
|---|---|---|
| | Calculated mass | Observed mass |
| 1. | 765.8 | 766.3 [M]⁺ |
| 2. | 765.8 | 766.4 [M]⁺ |
| 3. | 751.8 | 752.2 [M]⁺ |
| 4. | 807.9 | 808.5 [M]⁺ |
| 5. | 731.8 | 732.3 [M]⁺ |
| 6. | 791.9 | 792.3 [M]⁺ |
| 7. | 777.9 | 778.8 [M + H]⁺ |
| 8. | 717.8 | 718.4 [M + H]⁺ |
| 9. | 791.9 | 792.4 [M]⁺ |
| 10. | 777.9 | 779.4 [M + H]⁺ |
| 11. | 803.9 | 804.6 [M + H]⁺ |
| 12. | 816.0 | 816.3 [M]⁺ |
| 13. | 796.0 | 796.4 [M]⁺ |
| 14. | 880.8 | 881.7 [M + H]⁺ |
| 15. | 994.0 | 994.8 [M + H]⁺ |
| 16. | 894.9 | 895.5 [M + H]⁺ |
| 17. | 1008.0 | 1008.6 [M + H]⁺ |
| 18. | 994.0 | 995.0 [M + H]⁺ |
| 19. | 994.0 | 994.8 [M + H]⁺ |
| 20. | 894.9 | 895.5 [M + H]⁺ |
| 21. | 781.8 | 783.3 [M + H]⁺ |
| 22. | 765.9 | 766.9 [M + H]⁺ |
| 23. | 766.8 | 767.5 [M]⁺ |
| 24. | 894.0 | 894.9 [M + H]⁺ |

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof. For example, the following compounds which can be prepared by following similar procedure as described above with suitable modification known to the one ordinary skilled in the art are also included in the scope of the present application:

TABLE 3

25

Ser-N(H)—C(=O)—[cycle with NH]—Thr-Ser-N(H)—C(=O)—Ser-D-Glu-NH₂

SE*TSK*SE {C-terminus Glutamic acid is D- Glu}
(SEQ ID NO: 27)

26

Glu-N(H)—C(=O)—[cycle with NH]—Met-Ser-N(H)—C(=O)—Val-Ile-NH₂

(SEQ ID NO: 28)

27

H₂N—C(=O)—[cycle with NH]—Asn-Thr-Ser-N(H)—C(=O)—Ser-Phe-NH₂

(SEQ ID NO: 29)

28

Ser-Asn-N(H)—C(=O)—[cycle with NH]—Ser-Ser-Phe-N(H)—C(=O)—NH₂

(SEQ ID NO: 30)

29

Ser-Asn-Thr-N(H)—C(=O)—[cycle with NH]—Glu-Ser-Phe-N(H)—C(=O)—NH₂

(SEQ ID NO: 31)

30

H₂N—C(=O)—[cycle with HN]—Asn-Thr-Ser-N(H)—C(=O)—Ser-Phe-NH₂

(SEQ ID NO: 32)

TABLE 3-continued

31
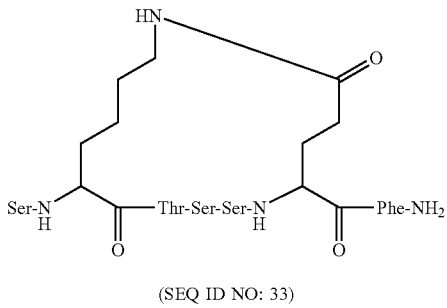
(SEQ ID NO: 33)

32
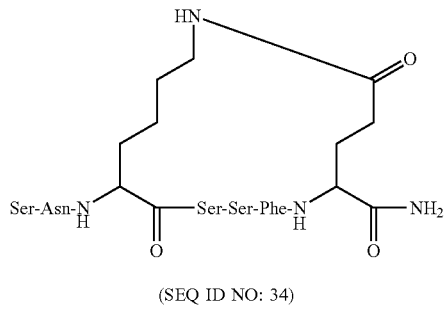
(SEQ ID NO: 34)

33
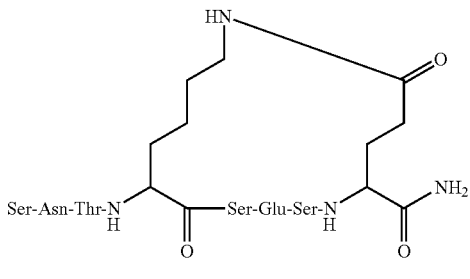
(SEQ ID NO: 35)

34
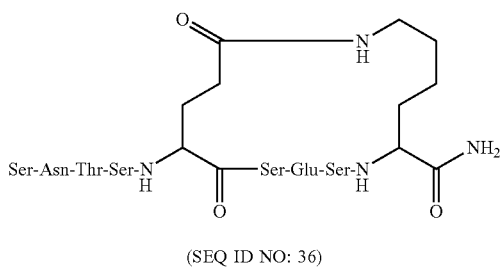
(SEQ ID NO: 36)

Use of MDA-MB-231 Cells as a Source of PD-L1:

MDA-MB-231 cells were found to express PD-L1 by RT-PCR and FACS assays and therefore used as a source of PD-L1 in the assays.

Example: 8

The effect of PD1 derived peptides on mouse splenocyte proliferation inhibited by PDL1/PDL2 or tumor cells expressing PDL; analyzed by Fluorescence Activated Cell Shorting (FACS) method using CFSE labeling.

Requirement:

Mouse splenocytes harvested from 6-8 weeks old C57 BL6 mice; RPMI 1640 (GIBCO, Cat #11875); DMEM with high glucose (GIBCO, Cat # D6429); Fetal Bovine Serum [Hyclone, Cat # SH30071.03]; Penicillin (10000 unit/ml)-Streptomycin (10,000 µg/ml) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #—A10492); Histopaque (density-1.083 gm/ml) (SIGMA 10831); Trypan blue solution (SIGMA-T8154); 2 ml Norm Ject Luer Lock syringe—(Sigma 2014-12); 40 µm nylon cell strainer (BD FALCON 35230); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 µL of Di methyl Sulfoxide (DMSO $C_2H_6SO$, SIGMA-D-5879) and aliquoted in to tubes for further use. Working concentrations were titrated from 10 µM to 1 µM. (eBioscience—650850-85); 0.05% Trypsin and 0.02% EDTA (SIGMA 59417C); 96-well format ELISA plates (Corning CLS3390); BD FACS caliber (E6016).

Protocol

Splenocyte Preparation:

Splenocytes harvested in a 50 ml falcon tube by mashing spleen in a 40 µm cell strainer were further treated with 1 ml ACK lysis buffer for 5 mins at room temperature. After washing with 9 ml of RPMI complete media, cells were re-suspended in 3 ml of 1×PBS in a 15 ml tube. 3 ml of histopaque was added very carefully to the bottom of the tube without disturbing overlaying splenocyte suspension. Spin the tube at 800×g for 20 mins at room temperature. Opaque layer of lymphocytes was collected carefully without disturbing/mixing any of the layers. Cells were washed twice with cold 1×PBS followed by total cell counting using trypan blue exclusion method and used further for cell based assays.

CFSE Proliferation Assay:

CFSE is the abbreviation of Carboxyfluorescein Diacetate Succinimidyl Ester, a dye that passively diffuses into cells and binds to intracellular proteins.

Tumor cells were cultured and maintained in high glucose complete DMEM media. $1\times10^5$ tumor cells were plated in 96 well plates along with required conc. of PD1 derived peptide and allowed to adhere at 37° C. for 4 hrs. $1\times10^6$ cells/ml of harvested splenocytes were treated with 5 µM of CFSE in pre warmed 1×PBS/0.1% BSA solution for 10 mins at 37° C. Excess CFSE was quenched using 5 volumes of ice-cold culture media to the cells and incubated on ice for 5 mins. CFSE labeled splenocytes were further given three washes with ice cold complete DMEM media. CFSE labeled $1\times10^5$ splenocytes were added to above wells containing tumors cells and PD1 peptides. Splenocytes were stimulated with anti-CD3 and anti-CD28 antibody (1 µg/ml each) and the co-culture was further incubated for 72 hrs at 37° C. with 5% $CO_2$. Cells were harvested and washed thrice with ice cold FACS buffer and % proliferation was analyzed using a FACS caliber with 488 nm excitation and 521 nm emission filters. Each experimental condition was carried out in triplicates and each experiment at least carried out three times % splenocyte proliferation was analyzed using cell quest FACS program and fold induction was calculated by normalizing individual values to % background proliferation Fold Induction=% splenocyte proliferation/% background proliferation Stimulated splenocytes: Splenocytes+anti-CD3/CD28 stimulation Background proliferation: Splenocytes+anti-CD3/CD28+PDL or Tumor Compound effect was examined by adding required conc. of compound to anti-CD3/CD28 stimulated splenocytes in presence of ligand (PDL-1/PDL-2) or tumor cells.

TABLE 4

The effect of compounds on mouse splenocyte proliferation inhibited by PD1-PDL1 interaction in MDAMB231 over expressing PDL1

|  | % Splenocyte proliferation | Fold induction |
| --- | --- | --- |
| Background proliferation | 13 | 1.0 |
| Stimulated Splenocytes | 72 | 5.5 |
| Compound 1 | 60 | 4.6 |
| Compound 2 | 57 | 4.3 |
| Compound 4 | 36 | 2.8 |
| Compound 6 | 55 | 4.2 |
| Compound 7 | 52 | 4.0 |
| Compound 11 | 54 | 4.2 |
| Compound 12 | 39 | 3.0 |
| Compound 5 | 42 | 3.2 |
| Compound 14 | 55 | 4.2 |
| Compound 15 | 53 | 4 |
| Compound 16 | 36 | 2.8 |
| Compound 17 | 42 | 3.2 |
| Compound 20 | 36 | 2.8 |

Example 9

In Vivo Efficacy of Compound #2 on Lung Metastasis in B16F10 Subcutaneous Melanoma Model C57/Black6 female mice (Aurigene, Bangalore, India) aged 6 to 8 weeks were used for the experiment. Animals were acclimatized for a week in the experimental room before conducting the experiment. On day 0, B16F10 cells grown in DMEM containing 10% FBS at 70 to 75% confluency were harvested and $0.1 \times 10^6$ cells per animal were injected to mice subcutaneously on the right flank region. On day 1, peptide (Compound #2) at 5 mg/kg dose dissolved in PBS, pH 7.4 was dosed subcutaneously at the rate of 10 ml/kg volume for fourteen days once daily. Vehicle control group of mice received only saline. Taxol at 5 MPK (i.p) with qd dosing was used as reference in this study. Each group consisted of ten animals. Body weight and clinical signs were recorded daily. There was no body weight reduction during the period of dosing and no clinical signs observed. At the end of 14 days of dosing period lung was harvested and analysed for metastasis by counting the black nodules. It was observed that Compound 2 showed about 54 percent reduction in metastasis (FIG. 1).

The invention claimed is:

1. A peptide derivative of formula (I)

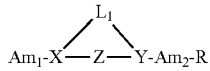

wherein,
Am$_1$ represents 1 to 4 amino acid residues which may be same or different and each independently selected from Ser, Val, Glu, Ile, Asn and Thr; or may be absent;
X is selected from Lys, Glu or Ser;
Y is Glu, Gln or Lys;
L$_1$ represents —CO—(CH$_2$)$_n$—NH—, —NH—(CH$_2$)$_n$—CO— or an amide bond between X and Y;
'n' is an integer selected from 1 to 5, both inclusive;
Am$_2$ represents 1 to 3 amino acid residues which may be same or different and each independently selected from Phe, Ser, Glu, Ile, Val, Gln, Tyr and Lys, or may be absent;
Z is Am$_3$-L$_2$;
L$_2$ is —NH—(CH$_2$)$_n$—CO— or is absent;
Am$_3$ represents 2 to 6 amino acid residues which may be same or different and each independently selected from Thr, Ser, Met, Glu, Asn, Phe and Lys;
R is an amidation of a C-terminal carboxylic acid moiety or is absent;
or a pharmaceutical salt of a peptide derivative of formula 1, or a stereoisomer of a peptide derivative of formula 1 or pharmaceutical salt thereof.

2. The peptide derivative according to claim 1, wherein one, more or all amino acids is/are in D-configuration.

3. The peptide derivative according to claim 1, wherein X is Lys.

4. The peptide derivative according to claim 1, wherein X is Glu.

5. The peptide derivative according to claim 1, wherein X is Ser.

6. The peptide derivative according to claim 1, wherein L$_1$ is —CO—(CH$_2$)$_5$—NH—.

7. The peptide derivative according to claim 1, wherein L$_1$ is an amide bond between X and Y.

8. The peptide derivative of claim 1 having the formula (Ia):

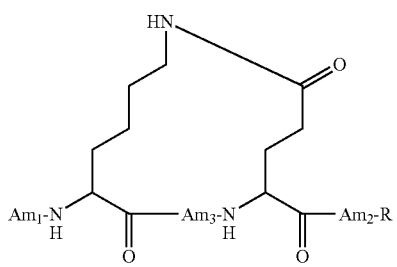

wherein,
Am$_1$, Am$_2$, Am$_3$ and R are same as defined in claim 1;
or a pharmaceutical salt of a peptide derivative of formula (Ia), or a stereoisomer of a peptide derivative of formula (Ia) or pharmaceutical salt thereof.

9. The peptide derivative according to claim 8, wherein Am$_1$ is Ser; Am$_3$ is Thr-Ser or Thr-Ser-Ser; Am$_2$ is Ser-Phe or Phe and R is an amidation of a C-terminal carboxylic acid moiety.

10. The peptide derivative according to claim 8, wherein Am$_1$ is absent; Am$_3$ is Asn-Thr-Ser; Am$_2$ is Ser-Phe and R is an amidation of a C-terminal carboxylic acid moiety.

11. The peptide derivative according to claim 8, wherein Am$_1$ is Ser-Asn; Am$_3$ is Ser-Ser-Phe; Am$_2$ is absent and R is an amidation of a C-terminal carboxylic acid moiety.

12. The peptide derivative according to claim 8, wherein Am$_1$ is Ser-Asn-Thr; Am$_3$ is Ser-Glu-Ser; Am$_2$ is absent and R is an amidation of a C-terminal carboxylic acid moiety.

13. The peptide derivative of claim 1 having the formula (Ib):

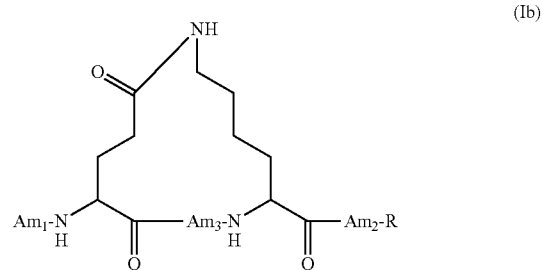

wherein,
Am$_1$, Am$_2$, Am$_3$ and R are same as defined in claim 1;
or a pharmaceutical salt of a peptide derivative of formula (Ib), or a stereoisomer of a peptide derivative of formula (Ib) or pharmaceutical salt thereof.

14. The peptide derivative according to claim 13, wherein Am$_1$ is Ser; Am$_3$ is Thr-Ser, Met-Ser or Thr-Ser-Ser; Am$_2$ is Ser-Phe, Ser-Ile, Val-Phe, Ser-Val, Ile-Phe, Ser-Tyr, Phe, Ser-DGlu or Ser-Phe-Lys and R is an amidation of a C-terminal carboxylic acid moiety or is absent.

15. The peptide derivative according to claim 13, wherein Am$_1$ is Ser-Asn-Thr-Ser; Am$_3$ is Ser-Glu-Ser; Am$_2$ is absent and R is an amidation of a C-terminal carboxylic acid moiety.

16. The peptide derivative according to claim 13, wherein Am$_1$ is Glu; Am$_3$ is Thr-Ser or Met-Ser; Am$_2$ is Ser-Phe or Val-Ile and R is an amidation of a C-terminal carboxylic acid moiety.

17. The peptide derivative according to claim 13, wherein Am$_1$ is Ile; Am$_3$ is Thr-Ser or Met-Ser; Am$_2$ is Ser-Phe, Ser-Gln or Val-Gln and R is absent.

18. The peptide derivative according to claim 13, wherein Am$_1$ is Val; Am$_3$ is Thr-Ser; Am$_2$ is Ser-Phe and R is an amidation of a C-terminal carboxylic acid moiety.

19. The peptide derivative according to claim 13, wherein Am$_1$ is Ser-Asn; Am$_3$ is Ser-Ser-Phe; Am$_2$ is absent and R is an amidation of a C-terminal carboxylic acid moiety.

20. The peptide derivative according to claim 13, wherein Am$_1$ is Ser-Asn-Thr; Am$_3$ is Glu-Ser-Phe; Am$_2$ is absent and R is an amidation of a C-terminal carboxylic acid moiety.

21. The peptide derivative according to claim 13, wherein Am$_1$ is absent; Am$_3$ is Asn-Thr-Ser; Am$_2$ is Ser-Phe and R is an amidation of a C-terminal carboxylic acid moiety.

22. The peptide derivative of claim 1 having the formula (Ic):

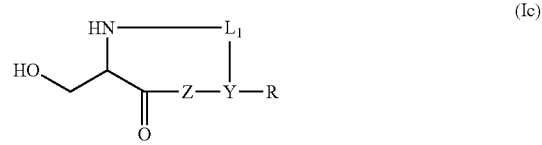

wherein,
Z is as defined in formula I;
Y is Glu or Gln;
$L_1$ is —CO—$(CH_2)_n$—NH— or an amide bond;
'n' is an integer selected from 2 to 5, both inclusive;
R is an amidation of a C-terminal carboxylic acid moiety or is absent;

or a pharmaceutical salt of a peptide derivative of formula (Ic), or a stereoisomer of a peptide derivative of formula (Ic) or pharmaceutical salt thereof.

23. The peptide derivative of claim 1 selected from the group consisting of

| Compound No | Structure |
|---|---|
| 1 | [Structure with Ser-NH, Thr-Ser-NH, Ser-Phe-NH$_2$, cyclic HN-containing ring] (SEQ ID NO: 3) |
| 2 | [Structure with Ser-NH, Thr-Ser-NH, Ser-Phe-NH$_2$, NH-containing chain] (SEQ ID NO: 4) |
| 3 | [Structure with OH, Asn-Thr-Ser-NH, Ser-Phe-NH$_2$, NH-containing chain] (SEQ ID NO: 5) |
| 4 | [Structure with Glu-NH, Thr-Ser-NH, Ser-Phe-NH$_2$, NH-containing chain] (SEQ ID NO: 6) |

| Compound No | Structure |
|---|---|
| 5 | 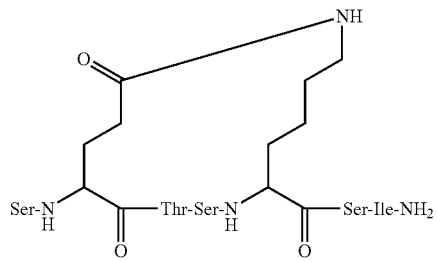(SEQ ID NO: 7) |
| 6 | 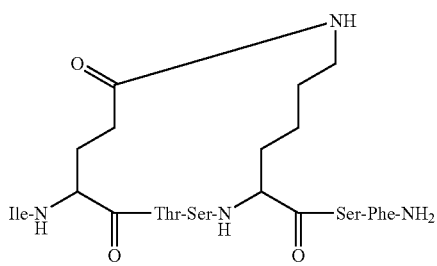(SEQ ID NO: 8) |
| 7 | 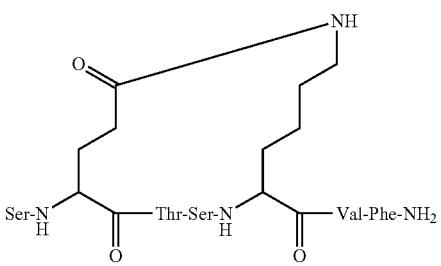(SEQ ID NO: 9) |
| 8 | 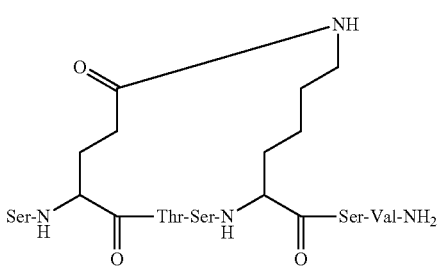(SEQ ID NO: 10) |
| 9 | 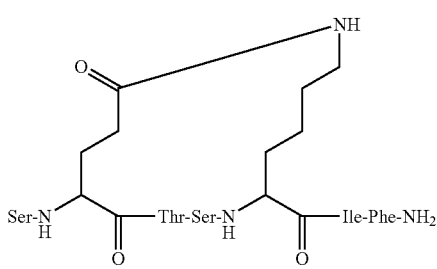(SEQ ID NO: 11) |

| Compound No | Structure |
|---|---|
| 10 | 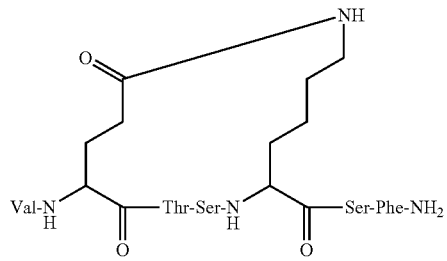<br>(SEQ ID NO: 12) |
| 11 | 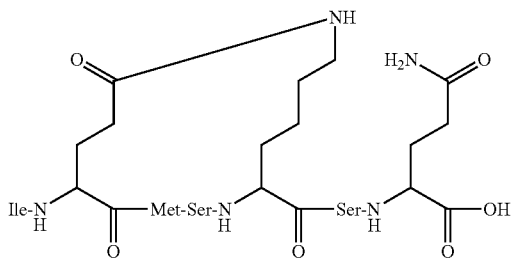<br>(SEQ ID NO: 13) |
| 12 | 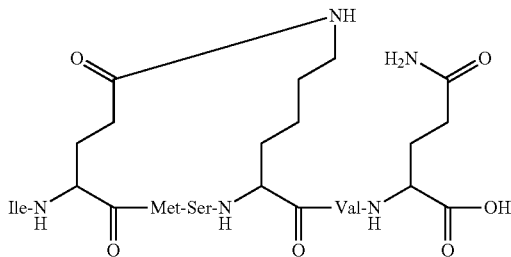<br>(SEQ ID NO: 14) |
| 13 | 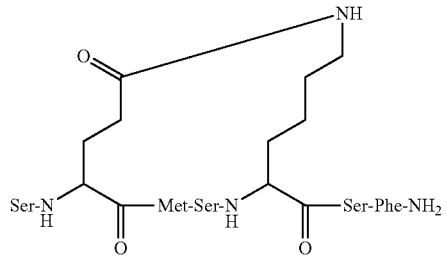<br>(SEQ ID NO: 15) |
| 14 | 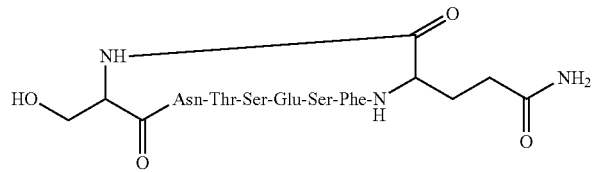<br>(SEQ ID NO: 16) |

| Compound No | Structure |
|---|---|
| 15 | 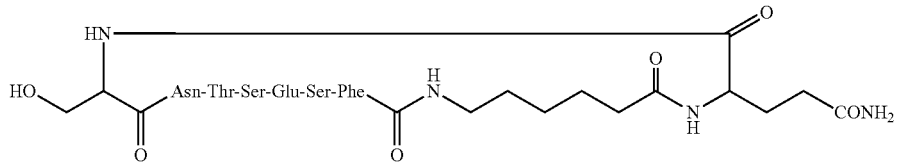<br>(SEQ ID NO: 17) |
| 16 | 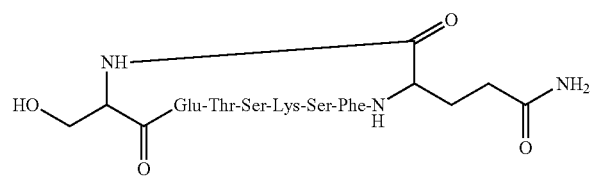<br>(SEQ ID NO: 18) |
| 17 | 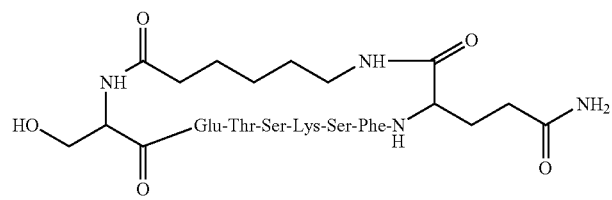<br>(SEQ ID NO: 19) |
| 18 | 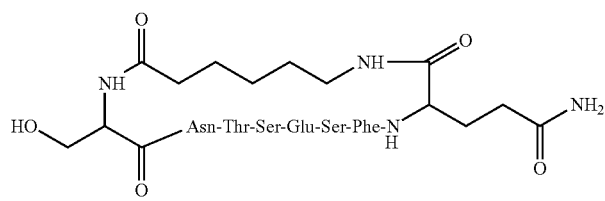<br>(SEQ ID NO: 20) |
| 19 | 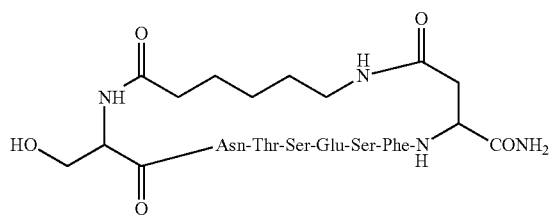<br>(SEQ ID NO: 21) |
| 20 | 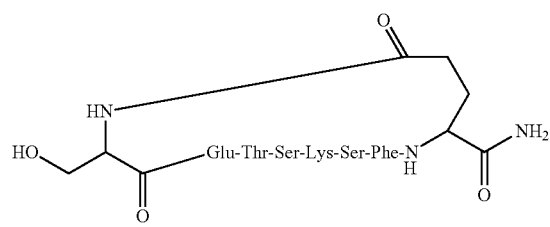<br>(SEQ ID NO: 22) |

| Compound No | Structure |
|---|---|
| 21 | 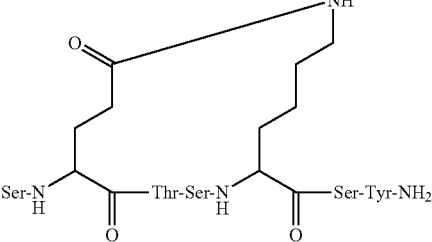<br>(SEQ ID NO: 25) |
| 22 | 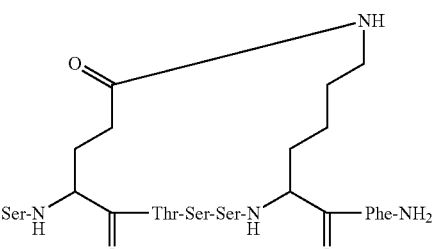<br>(SEQ ID NO: 26) |
| 23 | 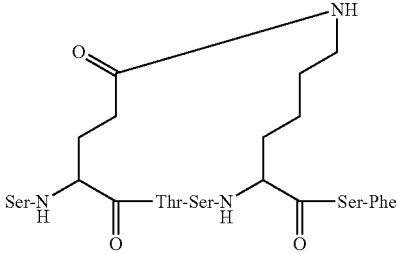<br>(SEQ ID NO: 27) |
| 24 | 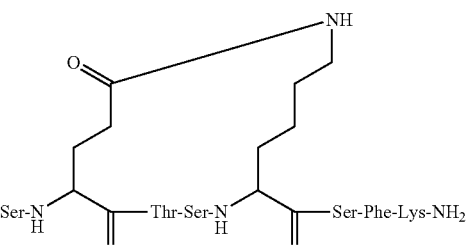<br>(SEQ ID NO: 26) |
| 25 | 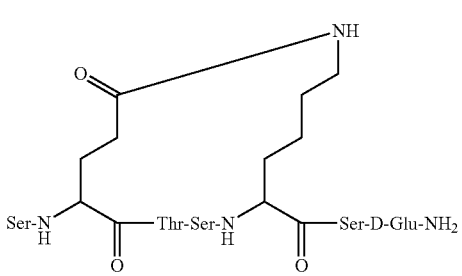<br>SE*TSK*SE {C-terminus Glutamic acid is D-Glu}<br>(SEQ ID NO: 27) |

| Compound No | Structure |
|---|---|
| 26 | 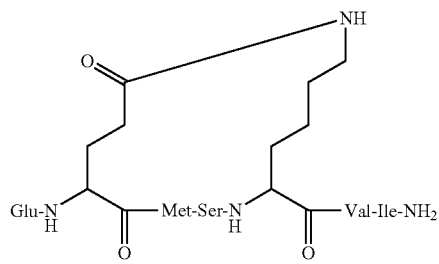<br>(SEQ ID NO: 28) |
| 27 | 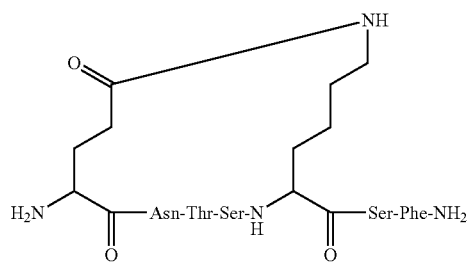<br>(SEQ ID NO: 29) |
| 28 | 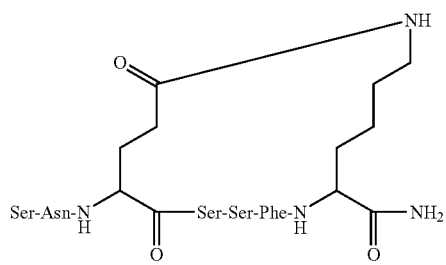<br>(SEQ ID NO: 30) |
| 29 | 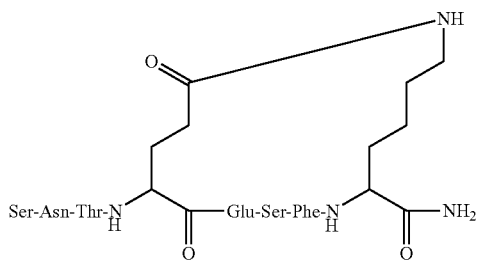<br>(SEQ ID NO: 31) |
| 30 | 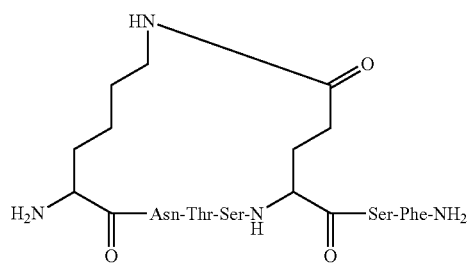<br>(SEQ ID NO: 32) |

| Compound No | Structure |
|---|---|
| 31 | 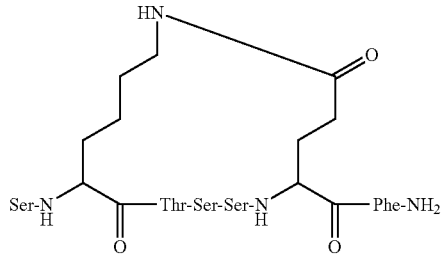<br>(SEQ ID NO: 33) |
| 32 | 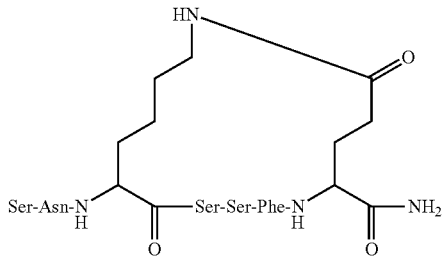<br>(SEQ ID NO: 34) |
| 33 | 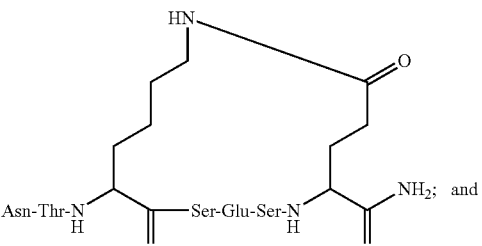<br>(SEQ ID NO: 35) |
| 34 | 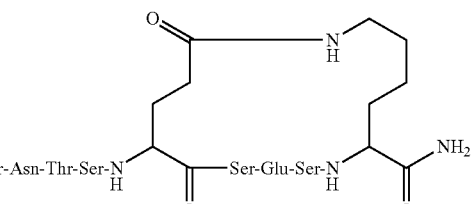<br>(SEQ ID NO: 36) | or a pharmaceutical salt thereof or a stereoisomer thereof.

24. A pharmaceutical composition comprising at least one peptide derivative according to claim 1, and/or a pharmaceutically acceptable salt or a stereoisomer thereof, and a pharmaceutically acceptable carrier or excipient.

25. The pharmaceutical composition of claim 24 further comprising at least one additional pharmaceutical agent wherein the said additional pharmaceutical agent is an anticancer agent, chemotherapy agent, or antiproliferative compound.

26. A method of modulating an immune response mediated by PD-1 signaling pathway in a subject, comprising administering to the subject therapeutically effective amount of the peptide derivative according to claim 1, such that the immune response in the subject is modulated.

27. A method of inhibiting growth of tumour cells and/or metastasis in a subject, comprising administering to the subject a therapeutically effective amount of the peptide derivative according to claim 1 inhibit the programmed cell death 1 (PD1) signaling pathway.

28. The method of claim 27, wherein the tumour cells are of a cancer selected from the group comprising of melanoma, renal cancer, prostate cancer, breast cancer, colon cancer and lung cancer.

29. The method of claim 27, wherein the tumour cells are of a cancer selected from the list comprising of bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

30. A method of treating an infectious disease in a subject comprising administering to the subject a therapeutically effective amount of the peptide derivative according to claim 1 to inhibit the programmed cell death 1 (PD1) signaling pathway such that the subject is treated for the infectious disease.

31. A method of treating bacterial, viral and fungal infections in a subject comprising administering to the subject a therapeutically effective amount of the peptide derivative according to claim 1 to inhibit the programmed cell death 1 (PD1) signaling pathway such that the subject is treated for the bacterial, viral and fungal infections.

* * * * *